US012303197B2

(12) United States Patent
Leahy et al.

(10) Patent No.: US 12,303,197 B2
(45) Date of Patent: May 20, 2025

(54) PATIENT TUNED OPHTHALMIC IMAGING SYSTEM WITH SINGLE EXPOSURE MULTI-TYPE IMAGING, IMPROVED FOCUSING, AND IMPROVED ANGIOGRAPHY IMAGE SEQUENCE DISPLAY

(71) Applicants: Carl Zeiss Meditec AG, Jena (DE); Carl Zeiss Meditec, Inc., Dublin, CA (US)

(72) Inventors: Conor Leahy, Dublin, CA (US); Jeffrey Schmidt, San Ramon, CA (US); Keith Brock, Oakland, CA (US); Priya Kulkarni, Pleasanton, CA (US); David Nolan, Petaluma, CA (US); Keith O'Hara, Pleasanton, CA (US); Matthew J. Everett, Livermore, CA (US); Michael Chen, Fremont, CA (US); Lars Omlor, Pleasanton, CA (US); Niranchana Manivannan, Fremont, CA (US); Mary Durbin, San Francisco, CA (US)

(73) Assignees: Carl Zeiss Meditec, Inc., Dublin, CA (US); Carl Zeiss Meditec AG, Jena (DE)

( * ) Notice: Subject to any disclaimer, the term of this patent is extended or adjusted under 35 U.S.C. 154(b) by 672 days.

(21) Appl. No.: 17/437,366

(22) PCT Filed: Mar. 18, 2020

(86) PCT No.: PCT/EP2020/057522
§ 371 (c)(1),
(2) Date: Sep. 8, 2021

(87) PCT Pub. No.: WO2020/188007
PCT Pub. Date: Sep. 24, 2020

(65) Prior Publication Data
US 2022/0160228 A1 May 26, 2022

Related U.S. Application Data

(60) Provisional application No. 62/821,283, filed on Mar. 20, 2019.

(51) Int. Cl.
*A61B 3/10* (2006.01)
*A61B 3/00* (2006.01)
(Continued)

(52) U.S. Cl.
CPC .............. *A61B 3/12* (2013.01); *A61B 3/0008* (2013.01); *A61B 3/14* (2013.01); *G06T 7/0014* (2013.01);
(Continued)

(58) Field of Classification Search
CPC ......... A61B 3/02; A61B 3/102; A61B 3/1025; A61B 3/113; A61B 3/1015; A61B 3/1225; A61B 3/024; A61B 3/005
(Continued)

(56) References Cited

U.S. PATENT DOCUMENTS

| 4,170,398 A | 10/1979 | Koester |
| 4,732,466 A | 3/1988 | Humphrey |

(Continued)

FOREIGN PATENT DOCUMENTS

| CN | 114364305 A | * | 4/2022 | ........... A61B 3/0058 |
| JP | 2011049401 A | * | 3/2011 | |

(Continued)

OTHER PUBLICATIONS

Akita et al., (1982). "A computer method of understanding ocular fundus images," Pattern Recogn, 15(6):431-443.
(Continued)

*Primary Examiner* — Dawayne Pinkney
(74) *Attorney, Agent, or Firm* — SNELL & WILMER L.L.P.

(57) ABSTRACT

An ophthalmic imaging system provides an automatic focus mechanism based on the difference of consecutive scan lines. The system also provides of user selection of a focus point within a fundus image. A neural network automatically identifies the optic nerve head in an FA or ICGA image, which may be used to determine fixation angle. The system also provides additional scan tables for multiple imaging
(Continued)

modalities to accommodate photophobia patients and multi-spectrum imaging options.

11 Claims, 24 Drawing Sheets

(51) Int. Cl.
    *A61B 3/02*         (2006.01)
    *A61B 3/12*         (2006.01)
    *A61B 3/14*         (2006.01)
    *G06T 7/00*         (2017.01)

(52) U.S. Cl.
    CPC ............... *G06T 2207/10048* (2013.01); *G06T 2207/10064* (2013.01); *G06T 2207/20084* (2013.01); *G06T 2207/20224* (2013.01); *G06T 2207/30041* (2013.01)

(58) Field of Classification Search
    USPC ........ 351/206, 200, 205, 209–210, 221–223, 351/245–246
    See application file for complete search history.

(56) References Cited

U.S. PATENT DOCUMENTS

| | | | |
|---|---|---|---|
| 6,549,801 | B1 | 4/2003 | Chen et al. |
| 6,741,359 | B2 | 5/2004 | Wei et al. |
| 7,284,859 | B2 | 10/2007 | Ferguson |
| 7,301,644 | B2 | 11/2007 | Knighton et al. |
| 7,794,081 | B2 | 9/2010 | Fujishiro et al. |
| 8,488,895 | B2 | 7/2013 | Muller et al. |
| 8,967,806 | B2 | 3/2015 | Bublitz et al. |
| 8,998,411 | B2 | 4/2015 | Tumlinson et al. |
| 9,078,602 | B2 | 7/2015 | Plaian et al. |
| 9,279,977 | B2 * | 3/2016 | Baranec ................. G01J 3/021 |
| 9,332,902 | B2 | 5/2016 | Tumlinson et al. |
| 9,456,746 | B2 | 10/2016 | Bublitz et al. |
| 9,700,206 | B2 | 7/2017 | An et al. |
| 9,706,915 | B2 | 7/2017 | Everett et al. |
| 9,759,544 | B2 | 9/2017 | An et al. |
| 10,674,909 | B2 * | 6/2020 | Kano ..................... G06T 7/11 |
| 2005/0171438 | A1 | 8/2005 | Chen et al. |
| 2009/0268160 | A1 | 10/2009 | Iwanaga et al. |
| 2010/0027857 | A1 | 2/2010 | Wang |
| 2011/0157348 | A1 | 6/2011 | Yamamoto |
| 2012/0277579 | A1 | 11/2012 | Sharma et al. |
| 2012/0307014 | A1 | 12/2012 | Wang |
| 2014/0232987 | A1 | 8/2014 | Westphal et al. |
| 2015/0131050 | A1 | 5/2015 | Bublitz et al. |

FOREIGN PATENT DOCUMENTS

| | | |
|---|---|---|
| JP | 2009-261573 | 11/2013 |
| WO | WO-2012059236 A1 | 5/2012 |
| WO | WO-2016124644 A1 | 8/2016 |
| WO | WO-2018178269 A1 | 6/2018 |

OTHER PUBLICATIONS

Alghamdi et al., (2016). "Automatic Optic Disc Abnormality Detection in Fundus Images: A Deep Learning Approach," OMIA 2016 Held in Conjunction with MICCAI 2016 Athens Greece, pp. 17-24.
Beach et al., (1999). "Oximetry of retinal vessels by dual-wavelength imaging: calibration and influence of pigmentation," Journal of Applied Physiology, 86(2):748-758.
Blazkiewicz et al., (2005). "Signal-to-noise ratio study of full-field Fourier-domain optical coherence tomography," Applied Optics, 44(36):7722-7729.
Calcagni et al., (2011). "Multispectral retinal image analysis: a novel non-invasive tool for retinal imaging," Eye, 25(12):1562-1569.
Delori et al., (2001). "Macular pigment density measured by autofluorescence spectrometry: comparison with reflectometry and heterochromatic flicker photometry," J. Opt. Soc. Am. A, 18(6):1212-1230.
Everdell et al., (2010). "Multispectral imaging of the ocular fundus using light emitting diode illumination," Review of Scientific Instruments, 81:093706, 10 pages.
Forest et al., (2002). "A review of laser scanning three-dimensional digitisers," IEEE International Conference on Intelligent Robots and Systems, pp. 73-78.
Gonzalez-Hernandez et al., (2018). "Segmentation of the Optic Nerve Head Based on Deep Learning to Determine its Hemoglobin Content in Normal and Glaucomatous Subjects," J Clin Exp Opthamol, 9(5):1000760, 8 pages.
Hammer et al., (2008). "Color Autofluorescence Imaging in Age-Related Macular Degeneration and Diabetic Retinopathy," Investigative Ophthalmology & Visual Science, 49(13):4207, 2 pages.
Heidelberg, (2007). "Spectralis HRA+OCT, Spectralis HRA, Spectralis OCT, Hardware Operating Instructions", Heidelberg Engineering GmbH, 001:19963, 27 pages.
Hillmann et al., (2011). "Holoscopy—holographic optical coherence tomography," Optics Letters, 36(13):2390-2392.
International Search Report and Written Opinion received for International Patent Application No. PCT/EP2020/057522 mailed on Jul. 29, 2020, 17 pages.
Mendels et al., (1999). "Identification of the optic disk boundary in retinal images using active contours," Proc. Irish Machine Vision Image Processing Conf, pp. 103-115.
Nakamura et al., (2007). "High-Speed three dimensional human retinal imaging by line field spectral domain optical coherence tomography," Optics Express, 15(12):7103-7116.
Niu et al., (2017). "Automatic localization of optic disc based on deep learning in fundus images," 2017 IEEE 2nd International Conference on Signal and Image Processing (ICSIP), pp. 208-212.
O'Connell et al., (2014). "Test-Retest Reliability of Retinal Oxygen Saturation Measurement," Optometry and Vision Science, 91(6):608-614.
Osaka, (1977). "Perceived brightness as a function of flash duration in the peripheral visual field," Perception & Psychophysics, 22(1):63-69.
Prahl, (1999). "Optical absorption of hemoglobin," available online at <http://omlc.ogi.edu/spectra/hemoglobin>, 4 pages.
Rangayyan et al., (2010), "Detection of the optic nerve head in fundus images of the retina with Gabor filters and phase portrait analysis," Journal of digital imaging, 23(4):438-53.
Ronneberger et al., (2015). "U-Net: Convolutional Networks for Biomedical Image Segmentation," Computer Vision and Pattern Recognition, arXiv:1505.04597, 8 pages.
Sekhar et al., (2008). "Automated localisation of optic disk and fovea in retinal fundus images," 2008 16th European Signal Processing Conference, Lausanne, 5 pages.
Sinthanayothin et al., (1999). "Automatic localisation of the optic disk, fovea, and retinal blood vessels from digital colour fundus images," Br. J. Ophthalmol., 83(8):902-910.
Stringham et al., (2003). "Action spectrum for photophobia," J. Opt. Soc. Am. A, 20(10):1852-1858.
Wüstemeyer et al., (2003). "Macular pigment density in healthy subjects quantified with a modified confocal scanning laser ophthalmoscope," Graefe's archive for clinical and experimental ophthalmology, 241(8):647-651.
Zhu et al., (2009). "Detection of the optic nerve head in fundus images of the retina using the Hough transform for circles," J Digit Imaging, 23(3):332-41.
Japan Patent Office; Japanese Office Action filed in Application No. 2021-556553 on Feb. 16, 2024.

* cited by examiner

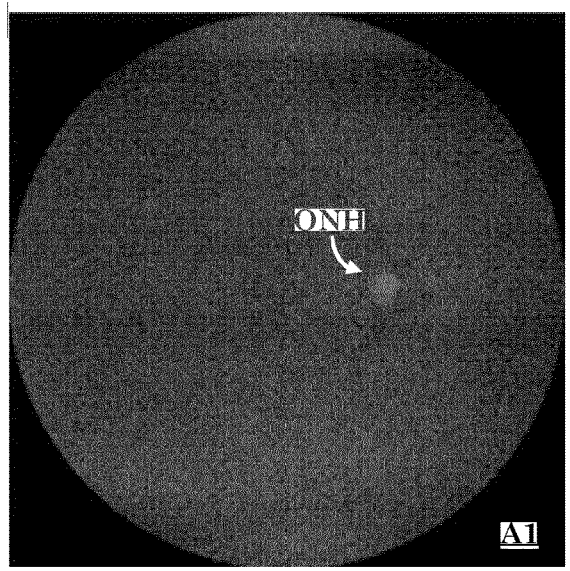
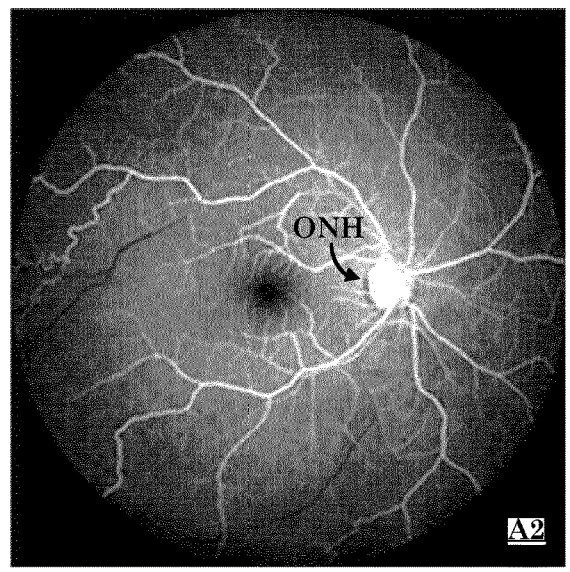
FIG. 5
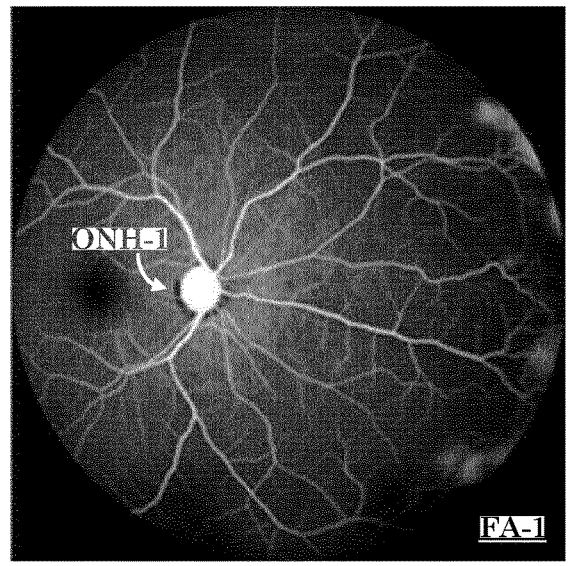
FIG. 7A          FIG. 7B

Sample Iris Color Table

| Iris Color | |
|---|---|
| Light | Red/Pink |
| | Blue |
| | Grey |
| | Green |
| Dark | Hazel |
| | Brown |

Intensity increases with darkening Iris Color →
← If image quality is poor, scan table increments intensity

Sample Pupil Size Table

| Pupil Size | |
|---|---|
| Large | <6 mm |
| | 5-6 mm |
| | 4-5mm |
| Small | 3-4mm |
| | 2-3mm |
| | <2 |

Intensity increases as pupil size shrinks →
← If image quality is poor, scan table increments intensity

PATIENT TUNED OPHTHALMIC IMAGING SYSTEM WITH SINGLE EXPOSURE MULTI-TYPE IMAGING, IMPROVED FOCUSING, AND IMPROVED ANGIOGRAPHY IMAGE SEQUENCE DISPLAY

PRIORITY

This application is a National Phase application under 35 U.S.C. § 371 of International Application No. PCT/EP2020/ 057522, filed Mar. 18, 2020, which claims priority to U.S. Provisional Application Ser. No. 62/821,283, filed Mar. 20, 2019, the contents of which are hereby incorporated by reference in their entirety.

FIELD OF INVENTION

The present invention is generally directed to the field of ophthalmic imaging systems. More specifically, it is directed to techniques for facilitating user operation of ophthalmic imaging system.

BACKGROUND

There are various types of ophthalmic examination systems, including ophthalmoscopes, Optical Coherence Tomography (OCT), and other ophthalmic imaging systems. One example of an ophthalmic imaging is slit-Scanning or Broad-Line fundus imaging (see for example U.S. Pat. Nos. 4,170,398, 4,732,466, PCT Publication No. 2012059236, US Patent Application No. 2014/0232987, and US Patent Publication No. 2015/0131050, the contents of all of which are hereby incorporated by reference), which is a promising technique for achieving high resolution in vivo imaging of the human retina. The imaging approach is a hybrid between confocal and widefield imaging systems. By illuminating a narrow strip of the retina while scanning, the illumination stays out of the viewing path, which enables a clearer view of much more of the retina than the annular ring illumination used in traditional fundus cameras.

To obtain a good image, it is desirable for the illuminating strip to be well-focused and to pass unabated through the pupil, and reach the fundus, of an eye. This requires careful focusing of the system and alignment of the eye with the ophthalmic imaging system. Further complicating ophthalmic imaging is that it can be difficult for a patient to remain still during imaging. This can be particularly problematic when multiple different types of images are needed or when the patient has an aversion to high intensity illumination, e.g., photophobia. Consequently, much training is generally needed to achieve a high level of competency in using such systems.

It is an object of the present invention to provide tools to facilitate the focusing of an ophthalmic imaging, or examination, system.

It is another object of the present invention to provide various methods to speed up the taking of ophthalmic images.

It is a further object of the present invention to provide methods for reducing patient anxiety, or discomfort, during the capturing of ophthalmic images.

SUMMARY OF INVENTION

The above objects are met in a system/method with improved focus and functionality. Firstly, a focus mechanism based on the difference between consecutive line scans effectively converts broad lines into thin lines for purposes of determining a defocus measure. These thin lines may further be used to determine the topology of the retina.

In a preferred embodiment, a system operator is presented with a preview screen that has multiple, predesignated focus aid locations. An image may be displayed on the preview screen, and the system operator may freely choose any point on the preview screen that should be brought into sharper focus. The preview screen then focuses the image at the chosen point by combining focus information from the focus aid locations.

In some embodiments, the focus is further adjusted based on the fixation angle of the patient. The fixation angle may be determined by locating the optic nerve head, (ONH) of the patient. Herein is provided a technique for identifying the ONH in an infrared (IR) preview image such that the patient's true fixation angle can be ascertained.

It is noted that identification of the ONH has additional uses, so identifying the ONH in any type of image is of benefit. Herein is presented a method determining the ONH in FA (fluorescence fundus angiography) and/or ICGA (indocyanine green angiography) images and/or any other imaging modality. Since the system may continuously capture IR (infrared) preview images prior to capturing an FA or ICGA image, the system locates the ONH in the IR preview image and then transfers the located ONH onto the captured FA or ICGA image.

To achieve this, the system provides a U-Net (a general description of a U-Net may be found in Ronneberger et al, "U-Net: Convolutional Networks for Biomedical Image Segmentation," Computer Vision and Pattern Recognition, 2015, arXiv:1505.04597 [cs.CV]), that uses transfer training in order to leverage a large library of training color images to learn how to locate the ONH in infrared images. The U-Net is first trained using only color images. Afterwards, a predefined number of initial layers of the U-Net are frozen, and the remaining layers are trained on a smaller training set of infrared images. Locating the ONH in infrared images can still be problematic, and so additional steps are provided to optimize ONH localization.

To further improve FA and ICGA examinations, the present system provides for simplified capturing of a sequence of FA or ICGA images. The present system provides a very high dynamic range such that an operator does not need to adjust image brightness while capturing an FA or ICGA image sequence. The raw images are stored and relative brightness information among the images in the sequence may be determined from the raw data and accurately provided to a user, for example, as a plot. Additionally, the operator is provided with options for brightening the stored images for viewing while maintaining the relative brightness between the acquired sequence of images.

To further accommodate a patient, the present system provides patient tuned imaging. The system examines the physical characteristics of a patient's eye (and or the patient's medical records) for indicator of photophobia. If a patent is suspected of being a candidate for photophobia, or is previously diagnosed with photophobia, the system operator is alerted to this fact. The system operator may then elect to let the system use a light-adjusted imaging scheme based on the patient's level of photophobia.

Other improvements in the present system include various mechanisms for taking multiple imaging modalities with a single capture command. This not only reduces the amount of time required for an examination, but also provides additional information that may be used for additional diagnosis. For example, along with every color image, the system may automatically capture an IR image, which can enhance the visibility of some tissues.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Any embodiment feature mentioned in one claim category, e.g. system, can be claimed in another claim category, e.g. method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIG. 5 provides two angio images taken at different phases of an angiography examination.

FIG. 7A illustrates the localization of an ONH region in an IR preview image identified using the system of FIG. 6.

FIG. 7B illustrates an FA image captured soon after capturing the IR preview image of FIG. 6.

DESCRIPTION OF THE PREFERRED EMBODIMENTS

There are various types of ophthalmic imaging systems, such as discussed below in sections Fundus Imaging System and Optical Coherence Tomography (OCT) Imaging System. Aspects of the present invention(s) may apply to any, or all, such ophthalmic imaging systems. In general, the present invention provides various enhancements to the operation and user interface of an ophthalmic imaging system.

Thin Line Scanning for Focus and Depth Analysis

One aspect of the present invention provides improved methods of determining image measures for focusing application (e.g., autofocus) and deconvolution applications (e.g., topography). As a particular example, the present enhanced focusing (and deconvolution) techniques and applications are described as applied to an ophthalmic imaging systems that use a linear light beam, such as a broad line, that is scanned across a sample to create a series of image-segments that can be combined to construct a composite image of the sample, but it is to be understood that the present invention may be applied to other types of ophthalmic imaging systems.

Figure 1:
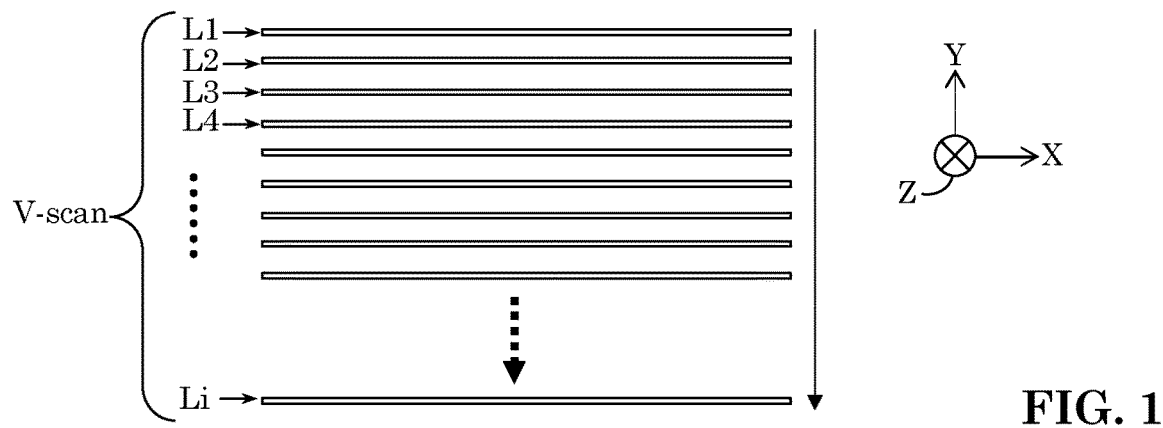
FIG. 1 illustrates a simplified pattern of scan lines as they may be produced on a subject being scanned.

For example, FIG. 1 illustrates a simplified pattern of scan lines (e.g., slits or broad lines) as they may be produced on a subject being scanned. In the present example, the scan lines are scanned (e.g., traversed) vertically to produce multiple scan lines L1 to Li in a vertical scan pattern, V-scan. Such a scan pattern may be used by a line scanning fundus imaging system (or OCT-based system), and in general, the scan lines may maintain some level of confocal suppression of out of focus light perpendicular (e.g., along the Y-axis) to the scan line (L1 to Li), but may lack confocal suppression along the line (e.g., along the X-axis). The scan lines may also be used to enhance imaging. For example, the sharpness of the edge of an illumination strip may be used to find an optimized focus for the line scanning system for the case where the illumination has not moved significantly during an acquisition by a detector (typically when the scan beam is being scanned in steps and is relatively motionless during an acquisition). Focusing methods suitable for line scanning fundus imaging systems are disclosed in international publication WO2018178269A1, herein incorporated in its entirety by reference. As another enhancement example, locations on the retina that are not directly illuminated by a scan line may be detected (e.g., image captured) to evaluate a background light level, e.g., stray light levels, coming from out-of-focus regions of the eye, and this background level may then be subtracted from a captured line image. Line scanning imagers have also been combined with pupil splitting (see for example Muller et al. U.S. Pat. No. 8,488,895, herein incorporate in its entirety by reference).

In summary, although a line scanning imaging system builds a fundus image by recording images of individual scan line on the retina of an eye, the recorded scan lines can be used to extract more information. For example, the line-width is a direct measure of focus. This information can be used to (e.g., auto) focus the system or as an additional input to deconvolution algorithms. Also, the line-position (center of mass) on the detector (e.g., camera) is a direct measure of the height of the sample (e.g., the depth of the retina at a particular point). This topography information can be used, for example, to analyze vessels, vessel-crossings, or other structures on top of the retina (like tumors to measure volumes).

One of the key technical details of line scanning is the line width. If the line is too broad it can be difficult, if not impossible, to separate the reflectivity from the position and the line width, and the localization uncertainty of the line increases, e.g., broad lines may automatically average the information over a large area. Although using broad lines to scan image has its benefits, as described below, broad lines might not be ideal for localization or width analysis. The present invention provides a method to exploit the scanning sequence to reduce the effective line-width, which can then be used for focus and/or topography analysis.

Figure 2A:
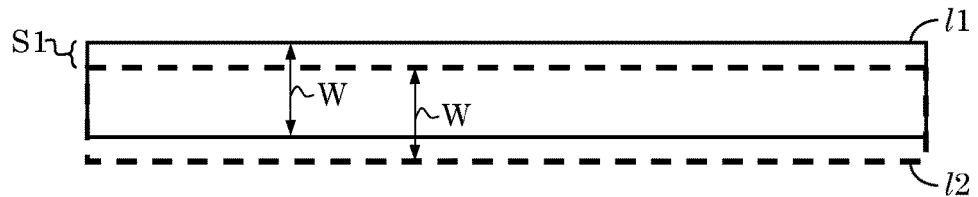
FIG. 2A illustrates an overlapping line scan sequence, where the step size between scan lines is smaller than the width of a scan line.
Figure 2B:
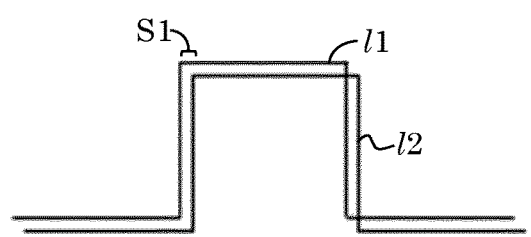
FIG. 2B illustrates the effects of subtracting two consecutively captured images of the consecutive scan lines of FIG. 2A.
Figure 2B:
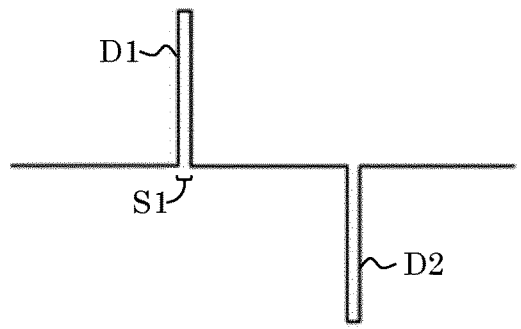

FIG. 2A illustrates an overlapping line scan sequence, where the step size between scan lines is smaller than the width of a scan line. For example, the scan step size S1 between a first scan line l1 and a second scan line l2 is smaller than the width W of scan line l1 (and scan line l2) such that the second scan line l2 overlaps a scan region defined by the first scan line l1. FIG. 2B illustrates the effects of subtracting two consecutively captured images (e.g., scan-images) of the consecutive scan lines (e.g., neighboring scan lines) of FIG. 2A (e.g., l2 subtracted from l1). The neighboring scan lines may be modeled as rectangles with a small displacement S1 that leads to a double line D1/D2 which has the width of the displacement S1. The two lines D1/D2 (one positive and the other negative) can now be analyzed according to their width S1 and location. This effectively converts a scan-image of a broad line (e.g., l1 and/or l2) with a small step-size S1, into a scan-image of a (double) thin line D1/D2 with the same step size.

To determine the line position of a captured scan-image, one may calculate the (light) intensity center of mass (e.g., a target region) of the captured scan-image. This is a very fast algorithm, but it may be susceptible to noise. To improve the robustness, the scan-image may be segmented into foreground and background (e.g., line and noise) segments, and the center of mass may be calculated for the foreground segment. The location of the center of mass can be calculated with a subpixel precision, which increases the depth sensitivity.

Figure 3A:
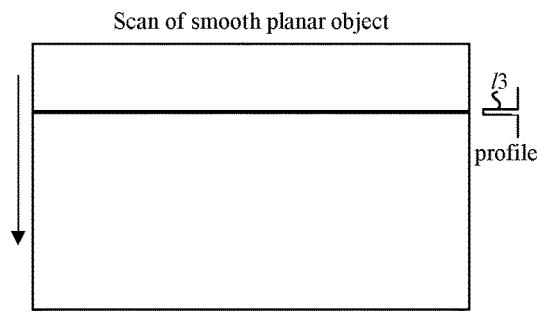
FIGS. 3A and 3B illustrate how the displacement of a center of mass may corresponds to a depth (or height) change (e.g., deconvolution measure) in an eye.
Figure 3B:
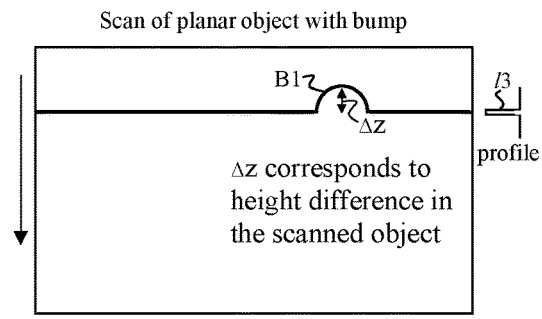

FIGS. 3A and 3B illustrate how the displacement of a center of mass may corresponds to a depth (or height) change (e.g., deconvolution measure) in an eye. The displacement (of the center of mass relative to an expected location) is a direct measure of the retinal topography and can be converted in a calibrated system into actual height (metrology). That is, a shift in location of a line position (from an expected position) may be due to a change in the height, or bump, of a scanned object (e.g., a change in the depth of the eye such as due to two vessels crossing each other). FIG. 3A shows a non-shifted scan-image of a scan line l3, such as from scanning a planar object with no irregularities in depth. FIG. 3B shows a scan-image of the same scan line l3 with a bump B1 due to the scanned object having an irregularity (e.g., bump) on its surface. The height Δz of the bump B1, which can be determined by following the change in position of the center of mass along the length of captured scan-image, corresponds to (e.g., is a measure of) the height of difference (bump) on the surface of the scanned object. This approach may benefit from calibration of the camera and the illumination optics.

In a similar fashion as the localization of the line position, the line width may be determined from the foreground segment using the second order moment (note: that the center of mass would correspond to the first moment) of the intensity distribution. The width is a direct measure of un-sharpness (e.g., defocus) of the image, at least in the direction orthogonal to the scan line. This width measure may be determined from either of the created thin lines illustrated in FIG. 2B.

Figure 2C:
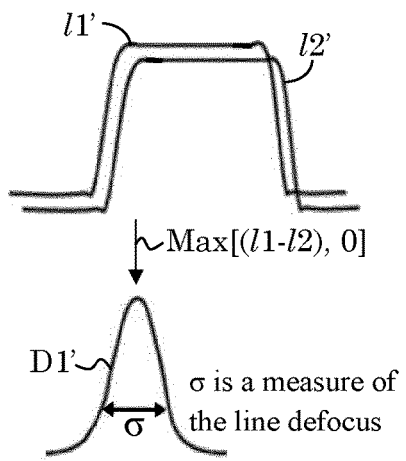
FIG. 2C illustrates the creation of a single thin line from two scan lines, and the identifying of the second order moment σ, which defines the line width.

For example, the double thin line D1/D2 may be converted into a single line by selecting one of the positive (e.g., D1) or negative (e.g., D2) lines for analysis. For instance, one may singularly define thin line D1 by choosing the maximum of (l1-l2) and setting the rest to zero (e.g., max [(l1-l2), 0]) or may singularly define thin line D2 by choosing the minimum of (l1-l2) and setting the rest to zero (min [(l1-l2), 0]). FIG. 2C illustrates the creation of a single thin line D1' from two scan lines l1' and l2' by defining max [(l1'-l2'), 0], and identifies the second order moment σ, which defines the line width of D1' and its location. Alternatively, or in addition to using the second moment σ, the line location and width may be defined by fitting a functional shape (e.g. a Gaussian) to the observed data (e.g. D1'). Then the location and width are given by the parameter of this fit. The advantage of this approach is that prior knowledge about the shape of the scan line (e.g. rectangular illumination) can be taken into account. In addition, a robust fit method can be used to decrease the noise sensitivity.

In this manner, broad lines in a fundus imaging system (such as those shown in FIG. 2A) may be converted (e.g., digitally) to thin lines as the difference of small stepped scan-images. The thin lines can then be analyzed with respect to the width (defocus) and location (object depth).

The line width and the line displacements are direct measures of defocus, which may be equated to the depth, i.e. the height, of the retina. These measures may be used internally by the imaging system, for example, to provide autofocus. With a higher resolution, such as described in reference to FIG. 2, it is possible to use this information for other purposes as well (e.g., depth can be used to segment vessels, to segment the optical disk, to estimate volumes of tumors, etc.). Essentially, the present method provides resolution enhancement.

The present resolution enhancement may be described by using the following imaging model:

$$\text{Image}=((\sqcap * p_{illum}) \cdot O) * p_{detect}$$

where Image is the observed intensities, $p_{illum}$ is the point spread function of the illumination, $p_{detect}$ is the point spread function of the detection, and $\sqcap$ is the rectangular stripe of the illumination. The asterisk symbol, *, denotes convolution and the dot, ·, denotes multiplication. This model is linear in the Illumination, which means:

$$\Sigma w_i \text{Image}=(((\Sigma w_i \sqcap_i) * p_{illum}) \cdot O) * p_{detect}$$

To improve the resolution, one may get rid of the term ($\Sigma w_i \sqcap_i) * p_{illum}$. The basic idea of subtracting the stripes is to transform the stripes into a delta peak: $\Sigma w_i \sqcap_i \approx \delta$. Simple subtraction gives two deltas but, as explained above, that is easily addressed by min-max operations. This minimizes the width of the illumination put into the imaging system, but still leaves the illumination blur as a limiting factor to the resolution ($\delta * p_{illum} = p_{illuim}$).

As an alternative, one may approximate a sine illumination using the weight $$\Sigma w_i \sqcap_i \approx \sin_i$$

This would lead to:

$$\sum w_i \text{ Image} =$$
$$(((\sin_i) * p_{illum}) \cdot 0) * p_{detect} = ((\alpha_i (\sin_i)) \cdot 0) * p_{detect} = a_i(((\sin_i)) \cdot 0) * p_{detect}$$

This is due to the fact that (complex) sinusoids are eigenfunctions for convolutions (e.g., sine/cosine convolved with something is a scaled sine/cosine). Now to remove the illumination blur, one may get rid of the alpha ($\alpha$) scaling factors, which deconvolves $p_{illum}$. After removing the alpha ($\alpha$) scaling factors, such as by intensity normalization, one can recombine the sinusoids (with inverse weights) and go back to either deltas or rectangles as illumination.

Using the present technique(s), a (unidirectional) defocus map may be constructed by determining the focus (and/or center of mass position) at multiple points along a scan-image, and the defocus map may then be used as an autofocus tool or to improve deconvolution algorithms.

Alternatively, instead of analyzing single scan lines, one may generate structured light pattern such as used in 3D scanning. Since the rectangular shape of the illumination is blurred (i.e. more Gaussian bell (or bump) shaped) it can be combined with alternating signs (e.g., positive and negative signs) to resample a sine-illumination. Three such patterns can be used for phase-shifting to extract depth information. Another example is the use of a triangular illumination pattern that can be approximated from rectangular patterns via correlations.

In the above example, the alpha ($\alpha$) scaling factors, which may be measures of amplitude (e.g., intensity), were gotten rid of to remove (or mitigate) the illumination blur, but it has been found that the alpha ($\alpha$) scaling factors change with (e.g., are representative of, or are related to) the defocusing of the illumination, and may therefore provide a direct measure of the defocus of the system. For example, a defocus measure may be determined based on the amplitude of sinusoid illumination. Furthermore, it has been found that the alpha ($\alpha$) scaling factors are frequency dependent. Consequently, using sinusoids of different frequencies leads to a series of alpha values that may be used to represent the complete (or substantially complete) point spread function of the system. Since the amplitude is dependent on the frequency used, one may also use the amplitude information to generate a pseudo modulation transfer function (MTF), which may include the system optics, the eye and the stripe-width. These alpha ($\alpha$) values may constitute "alpha maps" that may be used for autofocusing purposes and/or for depth measurement purposes (e.g., surface topography/topology). For example, since different frequencies result in different alpha ($\alpha$) values (e.g., different amplitudes), one may obtain a topography map by sweeping the frequency. The topography information may be determined by taking the Fast Fourier transform (FFT) of the amplitude data on a scan-by-scan basis. Thus, a topography and/or defocus map of the retina may be determined using a linear combination of image stripes (or scans).

Multi-Point and Balanced Auto Focus

Any of the above-described methods of determining defocus (or other known method of measuring defocus) at multiple points or locations on a fundus image (such as on a preliminary, or preview, image prior to imaging/scanning an eye) may be used with a graphical user interface (GIU) to enhance a user's (e.g., human operator's) ability to capture usable images of the fundus of the eye.

The depth of focus of widefield fundus cameras can be less than the variation in depth of the retina, causing the images to suffer peripheral defocus. This is seen quite frequently in images of myopic retinas. Also, in cases of retinal detachments and tumors the user can struggle to get an in-focus image on the tumor or raised retina, or on the surrounding retina. In traditional auto focus methods use in ophthalmic imaging systems, the (fundus) image is focused at the center of the image, but this does not help clinicians when they want to focus on a particular part (e.g., off-center) of the retina, or just wants to get an image with the best overall focus. The present invention addresses this problem.

Typically, auto focus is generally performed at the center of the field of view (FOV) of a camera using a number of different techniques. The limitation of this approach is that the focus is chosen purely based on the center of the image and thus cannot be used for areas not in the center of the field of view. This also prevents the imaging system from being able to bring more of the image into focus. As it would be understood, the back of an eye is not flat, and so different parts of an eye's fundus within a camera's FOV may require different focus settings to bring them into focus.

The present invention may determine focus at different parts of the eye, each part defining a focus aid location. The focus aid locations may then be used to determine an optimal focus for capturing a new image. The present invention may take focus readings at (e.g., determine defocus measures for)

multiple discrete locations (focus aid locations) in the eye using any of multiple focus aids/mechanism, e.g., as described above and/or in international publication WO2018178269A1. The focus at each location may be adjusted to compensate for various defocusing conditions (such as regions of astigmatism (irregularly shaped cornea) of the eye, floaters, curvature of the eye, etc.) to account for the fixating direction of the patient. Additionally, the system may adjust how an image is brought into focus in accordance with input instructions from a user (imaging system operator). For example, depending on how the user wants to focus an image (e.g., a balanced focus or focus at a point), weights for each of multiple focus aid locations may be calculated. Optionally, the gathered information may be combined to calculate a single focus reading. In this manner, the present invention may focus on any user-specified part of the eye, or bring a larger region of the imaging system's FOV into focus.

Figure 4A:
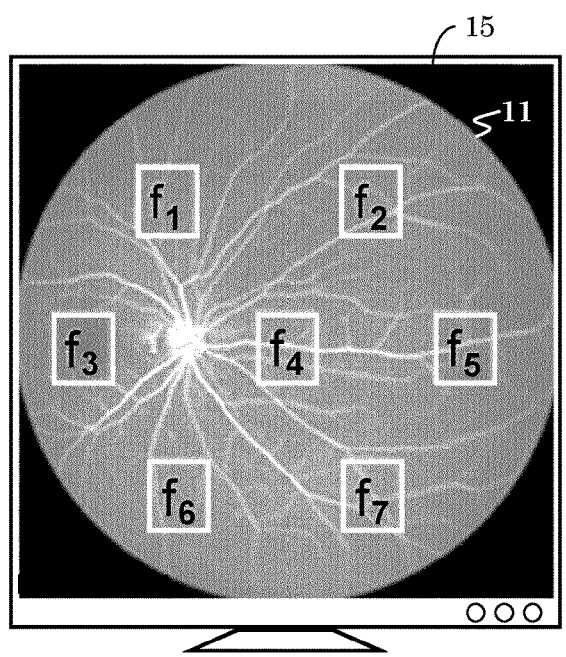
FIG. 4A illustrates a preview fundus image within a preview window on an electronic display, with multiple focus aid locations overlaid on the fundus image.

FIG. 4A illustrates a preview fundus image 11 within a preview window (or display region) 15 on an electronic display, with multiple focus aid locations $f_1$ to $f_7$ overlaid on the fundus image 11. It is to be understood that seven focus aid locations are shown for illustration purposes and that any number of multiple focus aid locations may be provided. It is further to be understood that focus aid locations $f_1$ to $f_7$ may be positioned at predesignated (and optionally fixed) locations and span a predefine area (fixed or variable) of the fundus image 11, or of the display region 15. Optionally, the focus aid locations $f_1$ to $f_7$ may be displayed on (e.g., overlaid over) the fundus image 11, or may be hidden from view in display region 15. That is, a user may be permitted to view and select any number of focus aid locations, $f_1$ to $f_7$, or the focus aid locations $f_1$ to $f_7$ may be hidden from view of the user. A user preferably selects one, or more, regions (or points) within fundus image 11 that should be brought into focus for capturing an image. The user may input this selection by use of any known input device, or mechanism, (e.g., a keyboard, pointer, roller, touchscreen, voice, input script, etc.)

In operation, each focus aid location on the retina (fundus) is illuminated (e.g., by a respective focus aid illumination, which may be a special scan line or other shape light beam) through an optical path entering the patient's pupil that is offset relative to the viewing path (e.g., collector path) of the imaging system's camera, as is explained below. Errors in the refractive power of a patient's eye bend the focus aid illumination entering the eye differently than the viewing path exiting the eye, resulting in a position of each focus aid location that depends on the refractive error (e.g. a position different than expected), and can be converted into a defocus measure of the system's camera relative to the focus setting needed for sharp imaging of the position of the focus aid illumination on the retina.

Figure 4B:
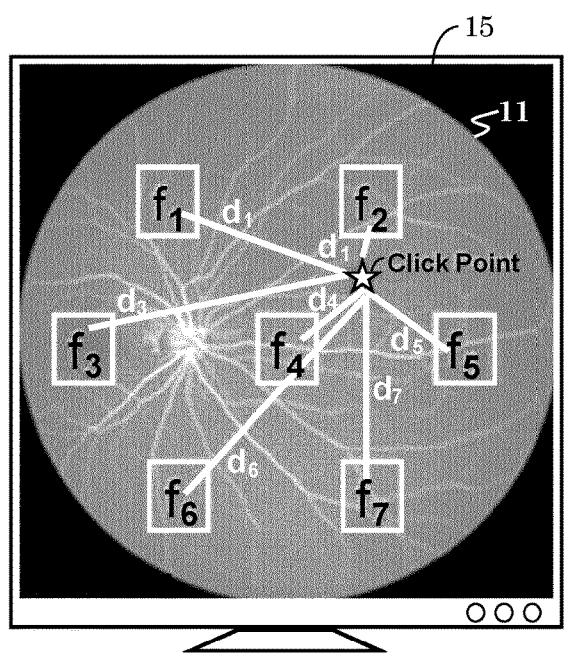
FIG. 4B provides an example of how a user may freely select any point(s) of the preview image to focus upon.

Each focus aid $f_1$ to $f_7$ senses the component of refraction in the direction of its offset in the pupil, which could be different from the refraction in other directions, and thus determines the focus for best image sharpness at its location, particularly when there is astigmatism. The average human eye has several diopters of astigmatism, and a fundus camera (or other ophthalmic imaging system) without adjustable astigmatism will typically only correct the astigmatism of the average eye when it is rotated to look centrally into the camera. When the eye is rotated relative to the camera, such as at any given fixation target, the present system can account for the misalignment between the astigmatism of the eye and the astigmatism-correction of the fundus camera. This may be done using the following formula:

$$f'_k = f_k + \left(H \times X_{Fixation} \times \left(X_{focus\ aid} + \frac{X_{Fixation}}{2}\right)\right) + \left(V \times Y_{Fixation} \times \left(Y_{focus\ aid} + \frac{Y_{Fixation}}{2}\right)\right)$$

where:
 $f_k$=The focus at a given focus aid location
 H=Horizontal Eye Orientation Factor
 $X_{Fixation}$=The X position of the Fixation Target
 $X_{focus\ aid}$=The X location of the focus aid
 V=Vertical Eye Orientation Factor
 $Y_{Fixation}$=The Y position of the Fixation Target
 $Y_{focus\ aid}$=The Y location of the focus aid Thus, the user may elect to optimize the system for focus at any given point/region within the system's FOV, such as by selecting a given focus aid location or any location on the preview fundus image 11. If a user-selected point/region for focusing does not corresponding to a specific focus aid location ($f_1$ to $f_7$), which may or may not be displayed on the preview image 11, the optimal focus for the user-selected point may be determined by an appropriate combination of weighted focus aids ($f_1$ to $f_7$) relative to the location of the user-selected point. Alternatively, user may elect to use a predefined balance of focus across the preview image, which may apply pre-defined weights for each of the focus aid locations. For example, a balance focus may be calculated as follows:

$$F = \frac{\sum_{k=1}^{N} w_k f'_k}{w_k}$$

where: $w_k$ = weight at focus location,
$f'_k$ = Astigmatism corrected focus at location FIG. 4B provides an example of how a user may freely select any point(s) of the preview image 11 to focus upon. In the present example, the user-input focus point is identified by a star. The user may input a desired focus point by use of an input device (e.g., a click point), or by use of a touch screen. In this case, an optimal focus for the user-input point may be determined as a weighted combination of the focus aid locations relative to the user-input point. For example, individual distances $d_1$ to $d_7$ from the input click point to respective focus aid locations $f_1$ to $f_7$ are determined. A focus for the click point (star) may then be determine as follows:

$$F = \frac{\sum_{k=1}^{N} w_k f'_k}{w_k}$$

where $$w_k \propto \frac{1}{d_k}$$

Where $d_k$=distance between the desired location of focus and a given focus aid location In summary, the present approach takes focus readings at multiple discrete locations on an eye (e.g., $f_1$ to $f_7$). The focus reading at each location is then adjusted to account for the fixating angle. Weights are calculated for each focus location relative to a user-input focus point (weights may be dependent upon the distance from a given discrete focus location to a user-selected focus point). Finally, a focus adjustment for the image capture may be calculated for the user-selected focus point based on the weighted focus of each discrete focus location.

It is noted that a system operator may provide a fixation point for a patient, but a patient might not be able to maintain focus on the provided fixation point. That is, a patient's true fixation point may differ from the system-provided fixation point. The present system may therefore further provide a mechanism for determining the patient's true fixation direction when determining optimal focus settings, as discussed above. For example, the system may use infrared imaging to obtain a test image, which may be the preview image 11. The system may then identify the optic nerve in the test (e.g., preview) image, and determine the patient's gaze angle based on the location of the identified optic nerve head. Identification of the optic nerve may be complicated if a patient suffers from optic nerve hypoplasia, which is typically associated with an underdeveloped optic nerve. The system may therefore further search for other landmarks indicative of gaze angle, such as the fovea or distinctive vasculature. The patient's gaze may then be determined in accordance with the location of the identified landmark in the IR preview image, and the known imaging settings (e.g. illumination and view angles) of the system relative to the patient's eye. Use of IR preview images is advantages since the eye is not sensitive to the IR wavelengths, and IR preview mages may be captured continuously without disturbing the eye, such as for system alignment purposes. The specific landmark may be identified by use of specific imaging processing algorithms or machine learning techniques (e.g., deep learning). Infrared (preview) images are preferred over visible light (preview) images for this task since landmarks in a visible light image may be more difficult to discern when taking particular types of images, such as fluorescence fundus (FA) or Indocyanine green angiography (ICGA) imaging. However, the identified location of the optic nerve head determined from the IR preview image may be applied directly to captured FA and/or ICGA images if the IR preview image is taken substantially close in time (e.g., immediately before or concurrent with) the captured FA and/or ICGA images. As it would be understood, the present use of IR imaging for determining the fixation angle of an eye may be used with other ophthalmic imaging systems, such as OCT. It is further noted that the IR image is herein used for fixation detection, and thus images the fundus (or back) of the eye, and not used for eye tracking, which images the pupil (or front) of the eye.

U-Net to Find Center of Optic Nerve Head in Widefield Fundus Images

Herein is provide an example of using deep learning to identify the center of the optic nerve head, such as in a widefield fundus image. As discussed above, the center of the optic nerve head may be used to identify a patient's gaze direction.

The optic nerve head (ONH) is one of the most prominent landmarks observed in fundus images, and the capability to automatically find the ONH is highly desirable in fundus image processing. An ONH locating algorithm could help find the fovea or other landmarks by providing a basis from which to apply a standardized offset or a region of interest (ROI) to start looking for pathology. Most of the available literature in ONH localization deals with locating the ONH in color (e.g., visible light) fundus images. However, there are several types of fundus images, and ONH localization techniques that are applicable to color images, many not lend themselves well to other types of images. For example, it is very difficult to localize the optic nerve in fluorescein angiography (FA) images and Indocyanine green angiography (ICGA) angiography images since the appearance of the ONH varies as a dye progresses through the eye vasculature during varies phases of the angiography examination. Herein is provided a U-Net based, deep learning, architecture applied to infrared (IR) preview images to find ONH robustly in all phases of FA and ICGA images.

Traditional ONH localization algorithms use hand-crafted features/filters. For example, "Automatic Localisation of the Optic Disk, Fovea, and Retinal Blood Vessels from Digital Colour Fundus Images," Br. J. Ophthalmol., vol. 83, no. 8, pp. 902-910, 1999 by Sinthanayothin et al. uses a variance filter to exploit the rapid variation in the intensity because of the presence of blood vessels in the Optic disc. This approach, however, works only with color fundus images and was tested on a small data set. It has also been shown that this approach is likely to fail for a fundus with white-colored lesions and prominent choroidal vessels. Another approach provided in "A Computer Method of Understanding Ocular Fundus Images," Pattern Recognition, Vol. 15, no. 6, 1982, pp. 431-443 by Akita et al. uses vessel tracking to localize the ONH. But this algorithm is dependent on the successful application of a vessel segmentation algorithm. Abnormal vasculature may lead to false-detection as the algorithm is reliant on the vasculature. Mendels et al. (in "Identification of the Optic Disk Boundary in Retinal Images Using Active Contours," in Proc. Irish Machine Vision Image Processing Conf., September 1999, pp. 103-115) uses active contours for ONH detection. A disadvantage of this approach is its dependency on the initial contour created by morphological filtering, which is not robust to variation in image quality. As the algorithm is based on active contours, it will also be less time efficient. Still another approach provided in "Automated Localisation of Optic Disk and Fovea in Retinal Fundus Images," 2008 16th European Signal Processing Conference, Lausanne, 2008, pp. 1-5, by Sekar et al. uses morphologiocal operations followed by the Hough transform to find the ONH. In this algorithm, the Hough transform is used to fit a circle with given limits of radius. The algorithm finds an image area with high gray level intensity variation and uses that as the basis for finding the ONH. Although this might not be a problem in normal images (e.g., images of healthy eyes), in images with pathologies, the optic disc might may not be the only structure with high intensity variations, which may lead to error. In "Detection of the Optic Nerve Head in Fundus Images of the Retina Using the Hough Transform for Circles," J Digit Imaging, 2009; 23(3):332-41 by Zhu et al., edge information and the Hough transform are used to find the ONH. However, this algorithm is likely not robust to variable image quality and ONH related pathologies as it is dependent on being able to extract good edge information (image quality) and match it to a circle of a certain radius. Another approach, described in "Detection of the Optic Nerve Head in Fundus Images of the Retina with Gabor Filters and Phase Portrait Analysis," Journal of digital imaging, 23(4), 438-53, by Rangayyan et al., uses Gabor filters to detected blood vessels and applies phase portrait modeling to try to locate the ONH. This algorithm is specifically based on the characteristic of the ONH as the point of convergence of retinal vessels. If the vessels or the nodes of convergence are obscured by image quality or pathology, the performance of this algorithm will be affected. Several approaches to using deep learning algorithms to locate the optic nerve using convolutional neural networks (CNN) have also been reported. A description of CNNs is provided below.

Examples of using CNNs to find the optic nerve are described in "Automatic Localization of Optic Disc Based on Deep Learning in Fundus Images," 2017 IEEE 2nd International Conference on Signal and Image Processing (ICSIP), Singapore, 2017, pp. 208-212, by D. Niu et al., "Segmentation of the Optic Nerve Head Based on Deep Learning to Determine its Hemoglobin Content in Normal and Glaucomatous Subjects," J Clin Exp Opthamol 9: 760 by Gonzalez-Hernandez D. et al., and "Automatic Optic Disc Abnormality Detection in Fundus Images: A Deep Learning Approach," Proceedings of the Ophthalmic Medical Image Analysis International Workshop (OMIA 2016 Held in Conjunction with MICCAI 2016 Athens Greece), Iowa Research Online, pp. 17-24, October, 2016, by H. S. Alghamdi et al. All of the above published works are herein incorporated in their entirety by reference. It is noted, however, that in all of these published works, the optic nerve head is detected in color fundus images. That is, all the of these approaches use features or train algorithm (in deep learning) using color fundus images (e.g., of the ONH).

The ONH locating approach of the present invention differs from the above examples in that it is suitable for locating the ONH in image types (e.g., imaging modalities) other than color images, such as in FA and ICGA images.

In an FA and an ICGA angiography examination, a series of time-lapse images are captured after injecting a light-reactive dye (e.g., fluorescent dye for FA and indocyanine green dye for ICGA) into a subject's bloodstream. High contrast images are captured using specific light frequencies selected to excite the dye. As the dye flows through the eye, various portions of the eye are made to glow brightly (e.g., fluoresce), making it possible to discern the progress of the dye, and hence the blood flow, through the eye. Portions with more dye will glow more brightly such that the series of captured imaged are typically characterized by being dark at first while no (or little) dye has entered the eye, growing in brightness as more dye enters and flows through the eye, and darken again as the dye exits the eye. Consequently, the appearance of the ONH varies over time as the dye progresses through vessels during varies phases of an angiography examination, which generally makes it very difficult to localize the ONH in fluorescein angiography (FA) and Indocyanine green angiography (ICGA) images. For illustration purposes, FIG. 5 provides two angio images, A1 and A2, taken at different phases of (or times during) an angiography examination. As shown the ONH in image A1 looks very different from the ONH in image A2, which complicates the creation of a filter suitable for all phases of an angiography examination. Thus, most of the available literature in ONH localization generally limit itself to color fundus images and avoids the difficulty of locating the ONH in FA or ICGA images. However, herein is presented a U-Net based, deep learning architecture applied to IR preview images to find the ONH robustly in all phases of FA and ICGA images, or any other type of image/scan.

Generally, an IR preview image of the fundus/retina is collected prior to taking a scan (image) for examination. As is explained above, the IR preview image may be used to adjust focus, and as is explained below, it may be used to assure accurate alignment of the system to the patient and to assure that the correct region of the eye will be imaged. Thus, an IR preview image is collected/recorded just before the capture of FA and/or ICGA images. It is herein put forth that the location of the ONH found in an IR preview image immediately before capturing an FA or ICGA image (or any other type of image) will be the same (remain unchanged) in the captured FA or ICGA image. That is, the location of the OHN in the IR preview image is used for ONH localization in FA and ICGA images. The present invention locates the OHN in FA and/or ICGA images indirectly by identifying the ONH in an IR preview image of the retina (using an algorithm trained using IR images) taken immediately prior to initiating capture of the FA and/or ICGA image, and transferring the location of the ONH from the IR preview image to the FA and/or ICGA image.

The previous, traditional approaches were limited to locating the ONH in color fundus images, and identifying the ONH in color fundus images is relatively straight forward (given substantial training images) as compared to locating the ONH in dynamic imaging modalities (imaging types) like FA and ICGA images. Collecting a substantial training image set (e.g., greater than 1000 images) for each of the various phases of FA and/or ICGA imaging is very difficult, particularly since this involves injection of light-reactive dye. The present invention circumvents some of these difficulties.

The present invention manages to locate the ONH (or any other predefined configuration or structure) without the need for a large amount of difficult to obtain angiography images (e.g., FA and/or ICGA images) to train a machine learning model. In one embodiment of the present invention, transfer training may be used to build on existing machine learning models trained to locate the ONH in color images by extending their operation to include IR images. Transfer learning is a machine learning method where a machine learning model developed for a first task is reused as the starting point for training another machine model on a second task. Pre-trained models are used as the starting point given the vast compute and time resources required to develop neural network models on these problems. For example, the present machine learning model can be trained using color images (or individual color channels extracted from color images) first and then transfer training to IR images. Use of transfer training is another novel feature of the present invention. For example, the present algorithm may be trained in two steps: first, trained using color images and/or color channels extracted from color images (e.g., about 2000 training images); and second, transfer training to IR images (e.g., about 1000 images). That is, an algorithm may be initially trained on color images and/or individual color-channel images (e.g., monochrome images), and then finish training on IR images. A reason for this this two-step approach may be if a large number of color images are readily available, as is the common case, (e.g. 2000 images a good quantity to train all the parameters in a neural network), and a smaller number of IR images are available for training. For example, red channel images extracted from color images may be used first to train the network in first step, and IR preview images may be used to transfer train the machine model on the same network. In this two-step approach, for example, after training the neural network using color images, a given number of early layers are frozen (e.g., their weight/parameters are frozen such that they do not change in subsequent training), and the neural network again only on its remaining unfrozen layers (or training only on a given number of last, e.g., two, layers) using IR preview images. Weight/parameter training in this second step is more limited than in the first step. However, since the availability of IR preview images is generally lower than that of color images, there may not be enough IR preview images to train all the weight/parameters in the network. For this reason, it is beneficial to train a machine model using commonly available modality images (e.g., color images) and freeze some layers, and then transfer train only a few layers of the neural network using the available IR preview images.

Alternatively, if a sufficient number of IR (preview) images are available for training (e.g., more than five thousand images), then the machine model may be trained on IR images alone, or on a combination of IR and color (or color-channel) images in one go (e.g., one training step). However, transfer training may still be used to boost performance since the color fundus images are generally more widely available than IR images. Experimentation has shown a measurable improvement in accuracy when using the present-step process, as compared to a one-step process.

Figure 6:
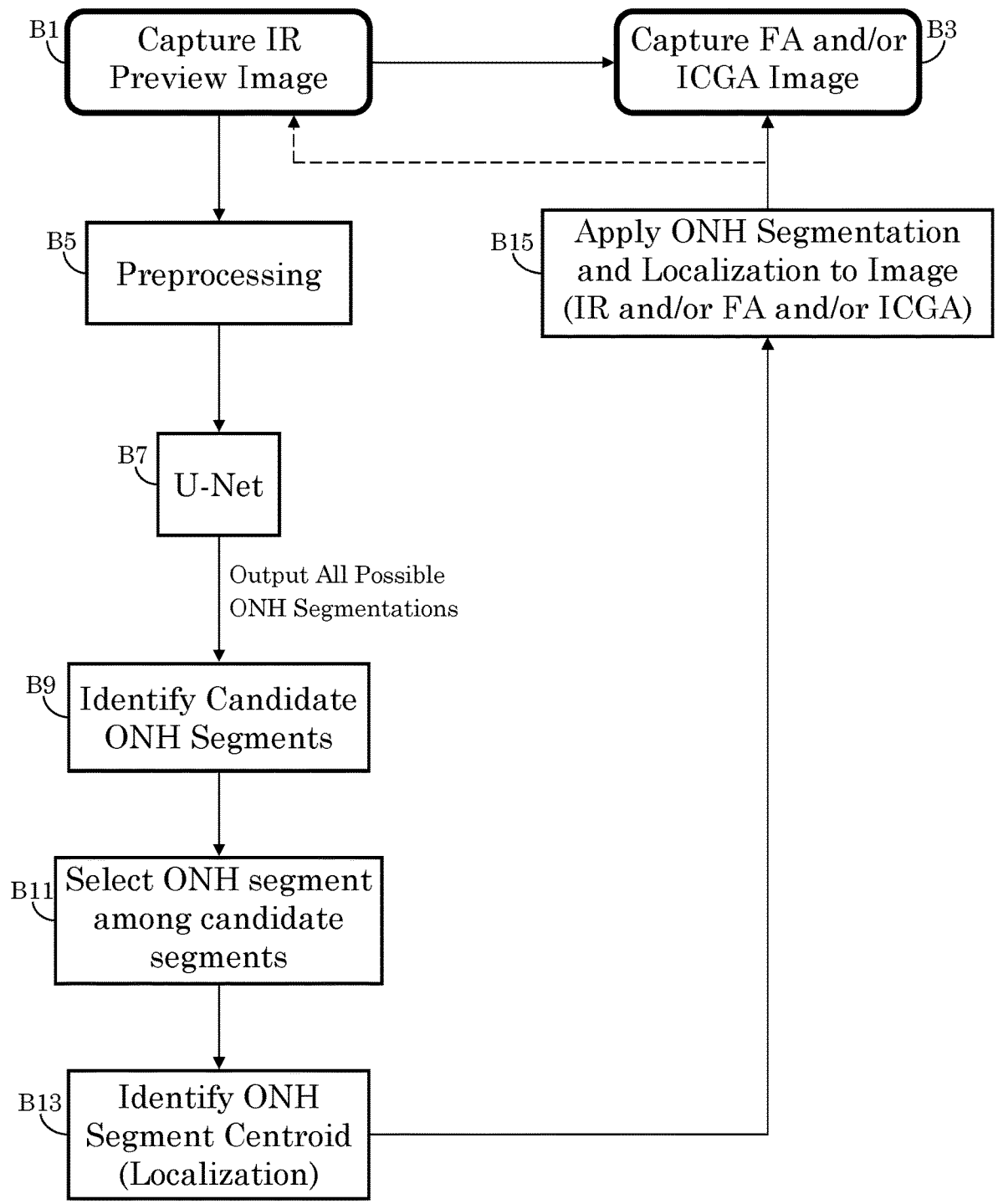
FIG. 6 provides a segmentation and localization framework for finding the ONH in FA/ICGA images in operation in accord with the present invention.

FIG. 6 provides a segmentation and localization framework for finding the ONH in FA/ICGA images in operation (in a deployed system) in accord with the present invention. The system may begin with block B1 by capturing an IR (e.g., preview) image, followed by capturing an FA and/or ICGA image in block B3. Alternatively in block B3, another type of image different from an IR image (e.g., FAF, color, etc.) may be taken in place of (or in addition to) the FA and/or ICGA image, and the present framework would likewise be effective for identifying the ONH in the other type of image. The captured IR image from block B1 may be submitted to an optional preprocessing block B5, which may apply an anti-aliasing filter and downsampling, prior to being submitted (as an input test image) to an already trained U-Net, deep learning, machine model, for processing (block B7).

An example of a suitable U-Net architecture is provided below. The U-Net of block B7 is trained to receive a test (IR) image and identify the ONH in the test image. Preferably, the U-Net is trained using a training set of IR fundus images (e.g., IR preview images) and a set of color fundus/channel-extracted color fundus in a two-step process, as discussed above. The U-Net may be trained first using color images and/or channel-channels extracted from color images using optic nerve head segments (e.g., image segments having the ONH demarcated such as by manual marking or by use of an automatic algorithm that identifies the OHN in the color images). This first training step assigns initial weights/parameter to all the layers of the U-Net. The resulting weights are transfer trained using IR preview images using optic nerve head segments generated from manual marking or an automatic algorithm. That is, the U-Net may be trained with some of its initial layers frozen at the initial weights/parameters and remaining unfrozen layers (e.g., last two layers) trained using the IR preview images. The U-Net thus receives a test (IR) image, and outputs a number of possible ONH segments identified within the test image.

Block B9 receives all the possible ONH segmentations identified by the U-Net and selects candidate ONH segments based on a size criteria. This criteria may include excluding all received ONH segments that are larger (e.g., in area or diameter) than a first threshold and smaller than a second threshold. The acceptable size range may be determined in accordance to a normative range.

The selected candidate ONH segments are then submitted to block B11, where one of the candidate ONH segments is selected as the true ONH segment. This selection may be based on the shape of the candidate ONH segments. For example, the candidate ONH segment having the roundest shape may be selected as the true ONH segment. This may be determined by taking a roundness measure of each candidate ONH region, such as by determining the difference between the minor and major axis (radius) of each candidate ONH segment. The ONH segment with the smallest difference between its minor and major axis may be selected as the true ONH segment. If multiple ONH segments are found to have the same roundness measure, then the largest among these may be designated the true ONH region.

With the true ONH segment thus identified, the next step is to determine its location within the IR (preview) image. The localization of the candidate ONH segment within the IR preview image may be made in by finding the centroid of the candidate ONH segment (block B13).

Finally in block B13, the identified ONH segmentation and localization may be applied to the captured IR preview image of block B1 and/or to the captured FA and/or ICGA image of block B3.

FIG. 7A illustrates the localization of an ONH region ONH-1 in an IR preview image IR-1 identified using the system of FIG. 6. FIG. 7B illustrates an FA image FA-1 (e.g., an angiography image) captured soon after capturing the IR preview image IR-1 of FIG. 6, e.g., image FA-1 is captured within a time period following the capture of image IR-1 determined to be short enough such that no substantial movement of the ONH is made by the eye. FIG. 7B shows the localized ONH region ONH-1 from image IR-1 transferred onto the FA image FA-1. In this manner, the ONH at any phase of an angiography examination (FA or ICGA) may be quickly and efficiently identified. Optionally, if supported by the imaging system, additional IR preview images may be continuously captured though multiple (or all) phases of the angiography examination such that the position of the ONH may be continuously updated, if needed, from the continuously captured IR preview images.

The captured sequence of FA or ICGA images may then be displayed with, or without, the identified ONH region highlighted. Irrespective, there are difficulties associated with displaying a series of captured FA or ICGA images.

Automatic Adjustment of an Angiography Image Sequences

Angiography imaging, both fluorescein angiography (FA) and indo-cyanine green angiography (ICGA), require capturing a wide range of light intensities ranging from dark to bright as an injected dye makes its way through the eye. Setting a camera to capture this change in intensity in a sequence of images can be difficult resulting in some images being saturated (e.g. too much signal gain causing overly bright, or washed out, images) or overly dim. Therefore, a system operator typically manually adjusts the camera's capture settings as the sequence of images for the FA or ICGA examination are being captured. For example, the system operator may monitor a currently captured image, and adjusts the camera to increase or decrease the gain for a subsequent image in the sequence of images. That is, most fundus cameras require the operator to adjust the illumination brightness, sensor gain, or aperture size during the angiogram to accommodate the diversity in signal level and try to capture images with good brightness for display (i.e., images that are not saturated or overly dim). This has several distinct disadvantages. A first disadvantage is that the operator's attention is distracted by the need to adjust camera settings (e.g., control brightness). A second disadvantage is that operator error or inaction can lead to under- or over-exposed images. A third disadvantage is that the resulting sequence of angiography images may be brightened differently from each other, meaning that the true variation in image intensity over time (which is indicative of the blood flow and may be relevant for assessing disease) is partially or completely obscured. Some ophthalmic imaging systems may provide automatic brightness control (or sensitivity control or automatic gain control) to reduce the burden of adjusting the camera from the system operator. This type of automatic control can help overcome the first and second disadvantages, but generally do not address the third disadvantage. Indeed, because automatic brightness control is typically applied on an individual image basis, all the images in the captured sequence may be individually adjusted to provide a similarly bright images. This would exacerbate the third disadvantage since it further hides the naturally-occurring, relative change in brightness between the images in the sequence.

The present invention provides an automatic adjustment of image brightness, while maintaining the true proportionate variation of signal intensity (among the different images) over the course of the angiogram examination. Additionally, the present invention may also provide a trend of light intensity level versus time, which may have clinical relevance for certain eye diseases.

Firstly, the present ophthalmic imaging system preferably captures an image sequence in an angiogram examination (e.g., FA or ICGA) using a high-dynamic range (photo) sensor. A novel feature of the present invention is the use of sensor with a dynamic range wide enough to avoid under-exposure and saturation during the capture of all images in the image sequence the angiogram examination without adjustment of the system/hardware (e.g., without adjustment to illumination brightness, sensor gain, and/or aperture size). The system stores the raw captured images (e.g., for future processing), but may optionally adjust each image for optical display without altering its raw data. The present system may interrogate regions of an image to determine an "image brightening factor" that optimally adjusts the image for best use of the display. The system may further interrogate the "image brightening factor" of every image acquired as part of an angiography series to determine a "sequence brightening factor" that adjusts all images in the series for best use of the display, with the constraint that the relative brightness between images within the series is maintained. In this case, the same "sequence brightening factor" may be applied to each image for display, rather than each image's individual "image brightening factor." Using the "sequence brightening factor" or the raw data, the present system may further determine and record a trend of image intensity level versus elapsed time since the dye injection.

The present system is optimized for angiography. It provides enough dynamic range to accommodate the range of fluorescence needed for angiography. Consequently, there is negligible risk of over-exposing an image, which obviates the need to ever adjust illumination intensity or detector sensitivity during the angiogram. Therefore, the operator is never distracted by the need to monitor or control the brightness or sensitivity of the image capture sequence. Because no adjustment is made to the photo sensor, the captured sequence of images, when reviewed by a doctor, faithfully represent the true relative changes in image intensity acquired throughout the angiogram, which is important in many diseases/pathologies. For example, vein or artery occlusions may slow the transit of the dye through the retina, meaning that the rate of fall-off in image intensity over time could be reduced. The relative difference in fluorescence between images is also important for diagnosing inflammatory conditions. By contrast, prior ophthalmic imaging systems obscure the true relative changes in image intensity due to adjustment of brightness or sensitivity settings, manual or automatic, during the data acquisition, and for which a doctor reviewing the images was likely not present.

Angiography image intensities vary widely depending on the transit phase of the dye, dosage of the dye, pigmentation of the retina, condition of the ocular media, and disease state. Most fundus imaging systems have limited dynamic range, and therefore may necessitate adjustment of illumination brightness or detector sensitivity settings during the angiogram to avoid under- or over-exposure. The natural variation of the fluorescent signal during the angiogram (which is usually strongest during the early phase, tailing off gradually into the late-phase), contains information about the transit dynamics of the blood through the retina, which may be useful to a clinician in assessing the health of the eye.

Figure 8:
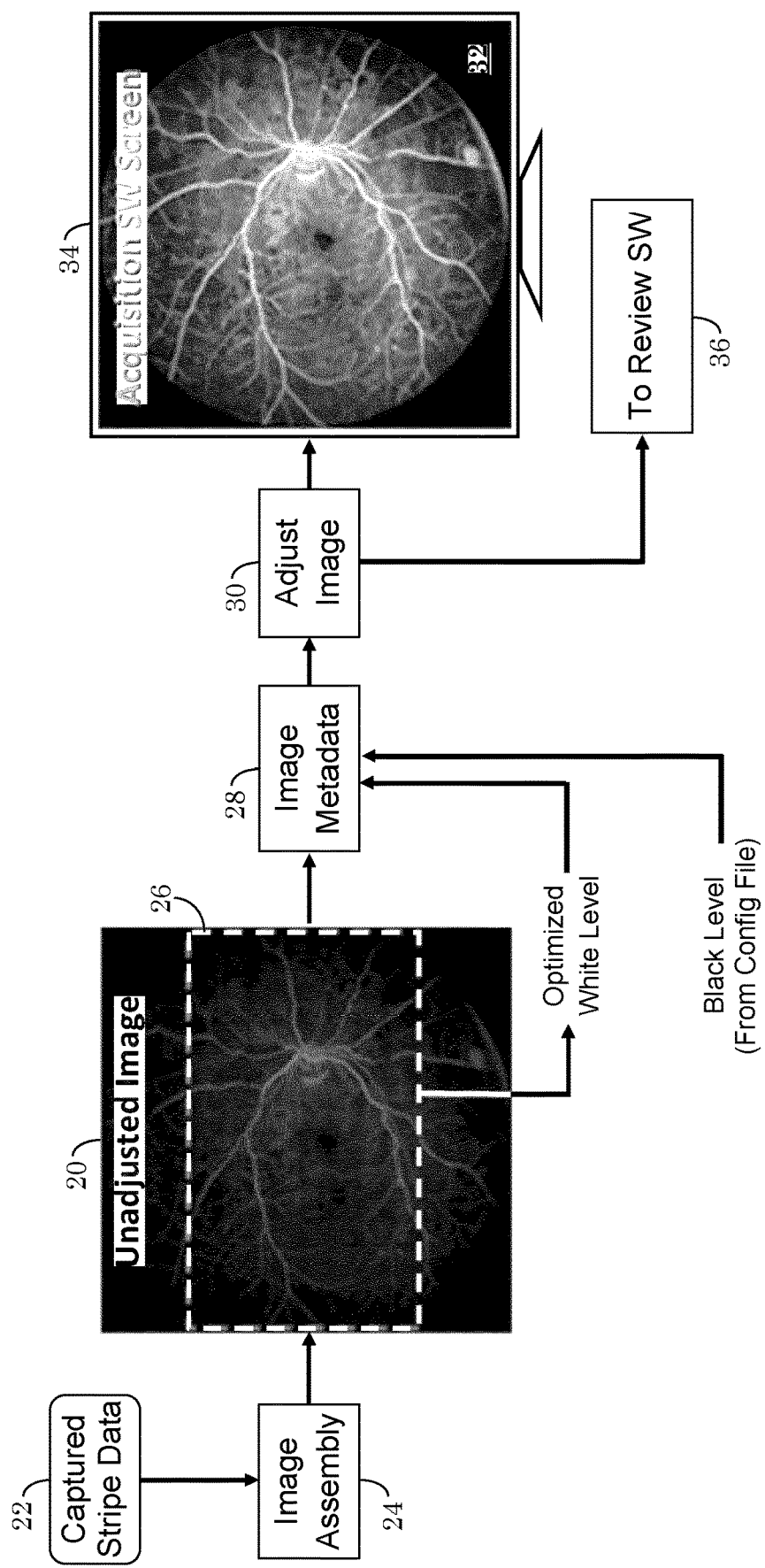
FIG. 8 provides a framework for processing individual images within a series of images captured as part of an angiogram examination.

FIG. 8 provides a framework for processing individual images within a series of images captured as part of an angiogram examination. If enabled by a system operator, such as by checking an "Auto-Adjust" checkbox in an acquisition window, during acquisition, captured images are optimized (in terms of gray-level range) for individual display (e.g., not for display as part of group or sequence of images representing a time lapse of the angiogram examination). This optimization prevents the individually displayed image from being too dark or over-saturated, which could hinder a technician from properly assessing image quality. First, an image 20 is captured. This may include capturing multiple scan lines (e.g., stripe data) 22 and montaging (assembling) 24 the stripe date into raw (unadjusted) image 20. For each image 20, the raw acquired pixel intensities are stored. An optimized white-level for displaying the image is determined for the raw image 20. The white-level may be determined by interrogating a part 26, or all, of the acquired image data 20, and calculating the 99.9th percentile (or some other appropriately chosen percentile) pixel intensity. The determined optimal white-level is stored in image metadata 28 associated with raw image 20. Also included in the metadata 28 is a black-level for displaying the image, which may be preset at a level to mask the electronic noise of the (photo) sensor, and which may be provided by a configuration file. Image metadata 28 effectively provides auto-brightening information for the individual image 20 (e.g., according to its white-level). The "image brightening factor" of an individual image 20 may be based on its individually determined white-level and/or black-level.

When an individual image 20 is selected for display, it undergoes image adjustment 30 (e.g., auto-brightening) according to its associated metadata 28 (e.g., according to its stored white-level and/or black-level). The adjusted image may then be output to a review screen 32 on an electronic display 34. Optionally, the adjusted image may also be sent to review software 36 for further processing.

Figure 9:
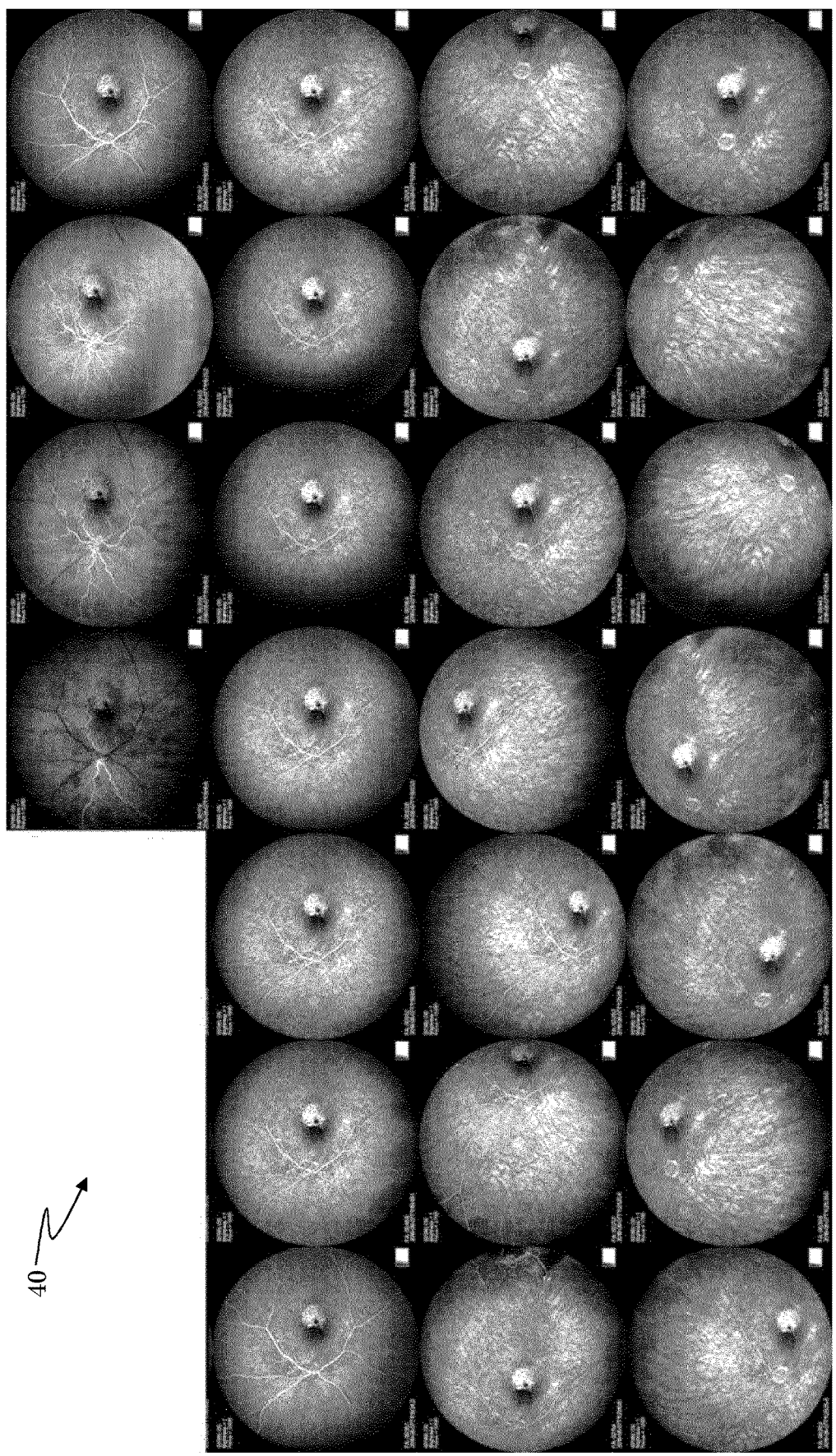
FIG. 9 shows an FA time-lapse image sequence with each individual image adjusted according to its respective individual white-level.

After all imaging is complete (e.g., all time-lapse images are captured) for a given angiogram examination, the time-lapse images may be displayed as a group. For example, the group images may be displayed on the review screen 32. Although each image's corresponding metadata provides information for individual display adjustment, displaying each image according to its individually optimized display settings would result in many of them having a similar appearance such that visual changes due to movement of the injected dye over time may not be easily discernable from one image to another. For example, FIG. 9 shows an FA time-laps image sequence 40 with each individual image adjusted (e.g., brightened) according to its respective individual white-level. Note that late-phases images appear similarly bright as early-phase images, despite the fact that a true fluorescence signal reduces over time, and late-phase images should therefore appear darker than early-phase images.

Figure 10:
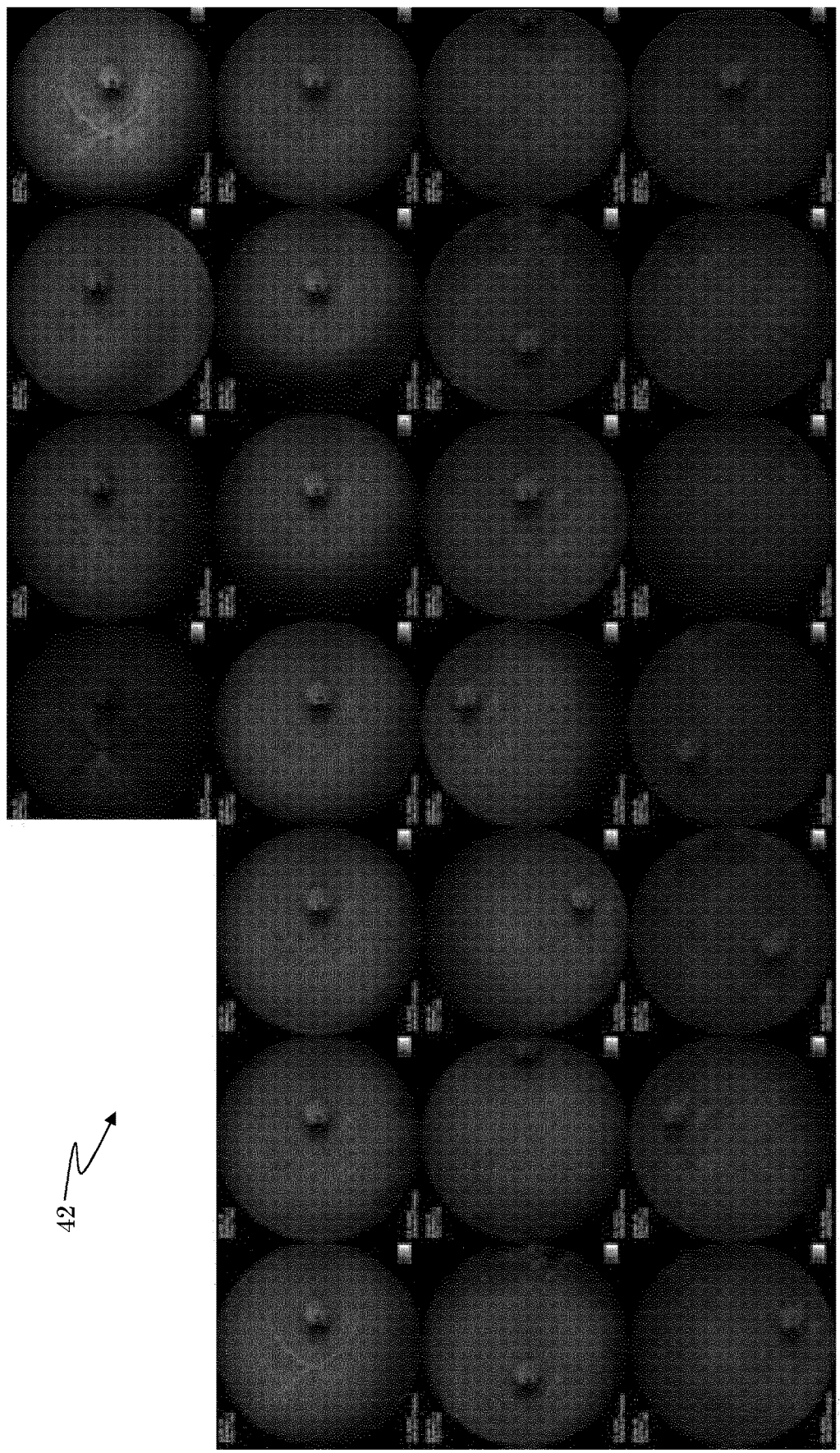
FIG. 10 shows a raw FA image sequence (corresponding to that of FIG. 9) with no brightness adjustment applied to any image.

The visual changes from one image to another due to dye transition are available in their respective raw data, but not in their respective display-optimized form. Displaying each image in a time-lapse sequence according to its raw data form would preserve the day transition information, but since no display optimization is applied, details in each image may be difficult to discern. For example, FIG. 10 shows a raw FA image sequence 42 (corresponding to that of FIG. 9) with no brightness adjustment applied to any image (e.g., displays each image's raw signal level). Consequently, many of the images are dim and difficult to assess.

Figure 11:
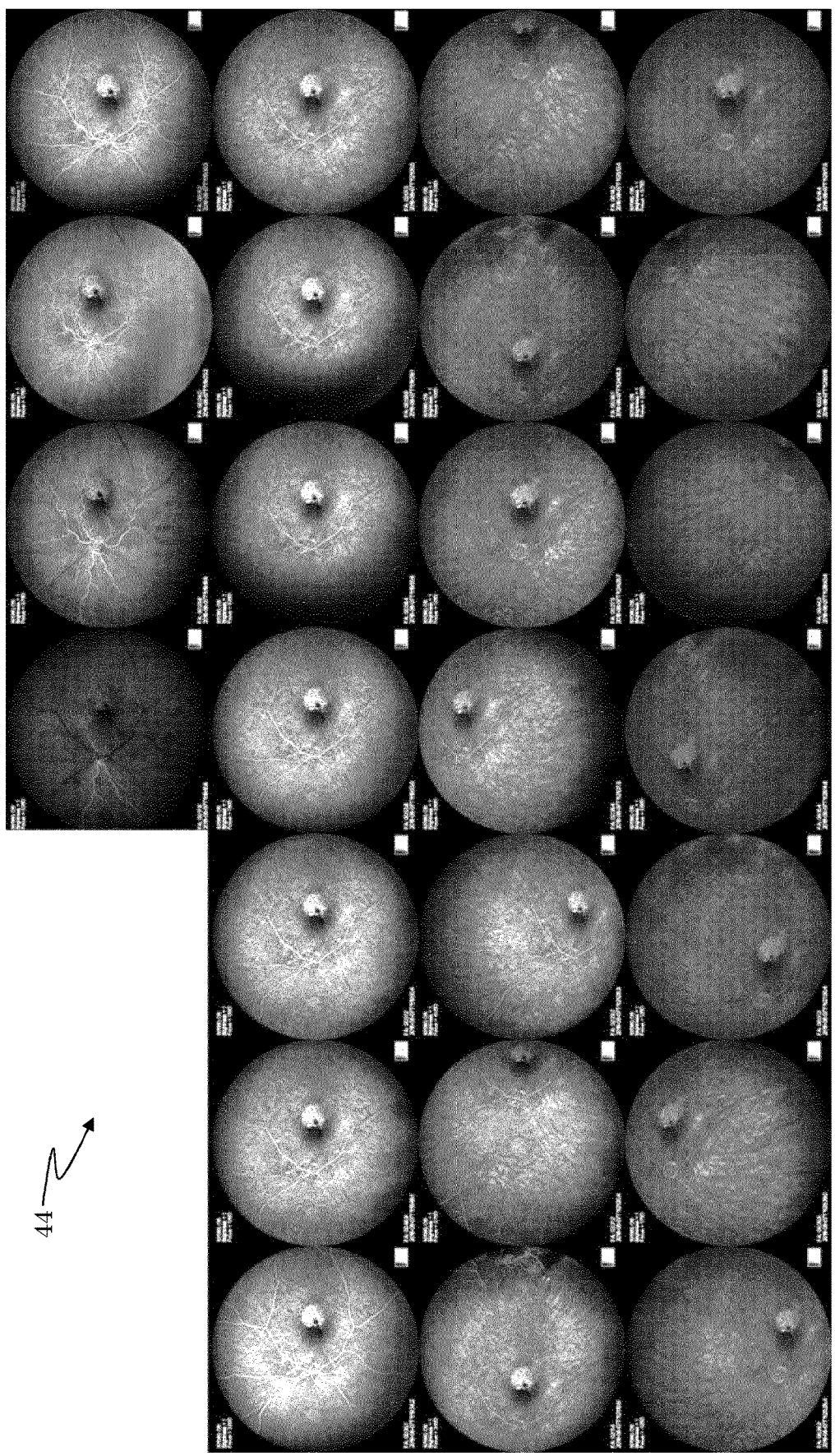
FIG. 11 shows a blanket-adjusted FA image sequence (corresponding to that of FIG. 10) with every image brightened by the same blanket scaling factor (e.g., 255/w max).

For a group display, a goal of the present invention is to adjust all images in the time-laps sequence, as a group, to display as much detail as possible while retaining the relative differences (e.g., visual changes) between individual images in terms of their overall brightness due to dye transition. Rather than auto-brightening all images in the sequence individually according to their respective white-levels (as illustrated in FIG. 9), one embodiment of the present invention examines the white-levels of all images (e.g., the white-level stored in each image's corresponding metadata) within the sequence and finds the maximum white-levels among them, which is herein termed "w max". A blanket scaling factor (e.g., a scaling factor spanning all images in the sequence) is defined as the maximum number of image intensity levels available divided by w max (e.g., 255/w max). This same blanket scaling factor is then applied to all images in the sequence such that the relative difference in brightness between images is preserved. FIG. 11 shows a blanket-adjusted FA image sequence 44 (corresponding to that of FIG. 10) with every image brightened by the same blanket scaling factor (e.g., 255/w max). As shown, the images preserve their relative intensity variations indicative of the true fluorescence signal, but unlike the raw FA image sequence 42 of FIG. 10, the images in FIG. 11 are brightened so as to optimize the visible detail.

In an alternate embodiment, rather than applying the same blanket scaling factor to all images in a sequence, each image may be individually adjusted based on its respectively stored white-level, but with its brightness setting adjusted in view of the group's w max. In this manner, the relative brightness of images in the sequence (e.g., group) is compressed so that they are generally brighter and easier to interpret, but still retain some semblance of the variation in fluorescence signal during the angiogram. This compression brightening technique can be implemented by applying a customized brightness scaling factor to individual images in the sequence, which may be computed as:

$$B(T) = \frac{255}{w(T)^{\propto} w_{max}^{1-\propto}}$$

where B(T) is the customized brightness scaling applied to an image acquired at time T during a time-lapse sequence of an angiogram examination, w(T) is the white-level of the image acquired at time T, $\propto$ is a compression parameter selected within a predefine range (e.g., in the range [0,1]), and w max is a blanket scaling factor, e.g., such as described above. Setting compression parameter $\propto=0$ is equivalent to applying the blanket scaling factor w max (without modification) as illustrated in FIG. 11, whereas setting $\propto=1$ is equivalent to auto-brightening the image according to its individually optimized display settings (without modification), as illustrated in FIG. 9.

The compression parameter $\propto$ may be set to a fixed value during an individual angiogram examination (e.g., preferably compression parameter $\propto$ is not changed during the acquisition of an image sequence), and ideally may be set to a value chosen by a clinician (e.g., system operator). That is, an input signal from the system operator may modify the amount of relative brightness compression between images in a sequence by adjusting the value of compression parameter $\propto$. For example, the system operator may adjust compression parameter $\propto$ by use of a brightness slide bar, by use of increment/decrement button(s), and/or by directly inputting a numerical value for $\propto$.

Figure 12A:
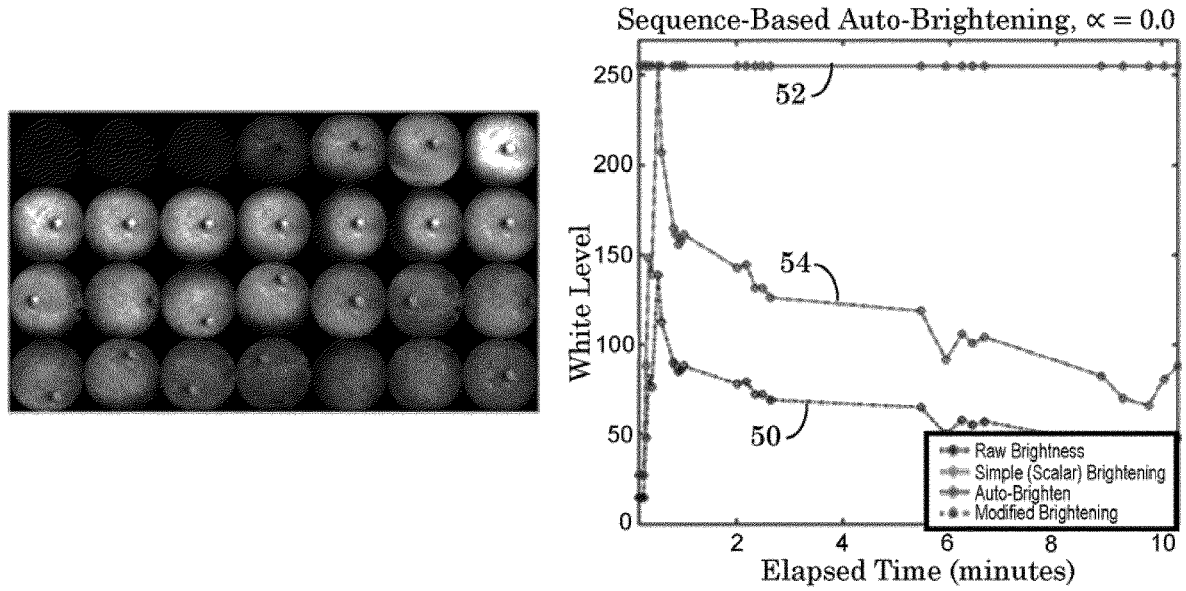
FIG. 12A illustrates the effects of compression parameter ∝ being set to zero, which is equivalent to brightening all the images by the same blanket scaling factor.

FIGS. 12A to 12F provide some examples of how this compression brightening technique affects the brightness of individual images in a time-lapse sequence for different values of compression parameter $\propto$. In each of FIGS. 12A to 12F, the resultant, brightened image sequence is shown on the left, and a plot of brightness versus elapsed time for the angiogram is shown on the right. In FIG. 12A, compression parameter $\propto$ is set to zero, which is equivalent to brightening all the images by the same blanket scaling factor, e.g., "w max" in the present case, as illustrated above in reference to FIG. 11. For comparison purposes, since the raw captured data is also stored, multiple plots are shown. Plot 50 illustrates the relative brightness between raw images over time (e.g., from zero to ten minutes) within the captured series of images. Plot 52 illustrates the relative brightness between images when each image is auto-brightness adjusted according to its stored white-level, which generally results in a similar brightness for the images. Plot 54 corresponds to the relative brightness between images when all are brightness adjusted according to the same w max value. As shown, the relative difference of w max plot 54 follows that of raw image plot 50.

Figure 12B:
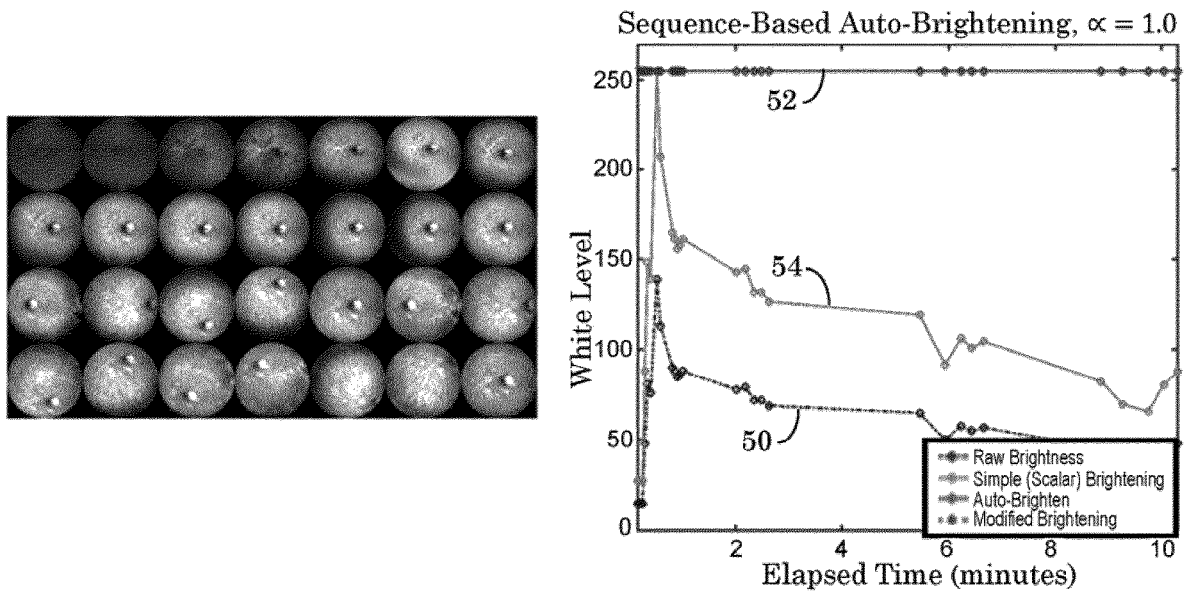
FIG. 12B illustrates the effects of compression parameter ∝ being set to one, which is equivalent to auto-brightening each image individually according to its stored white-level.
Figure 12C:
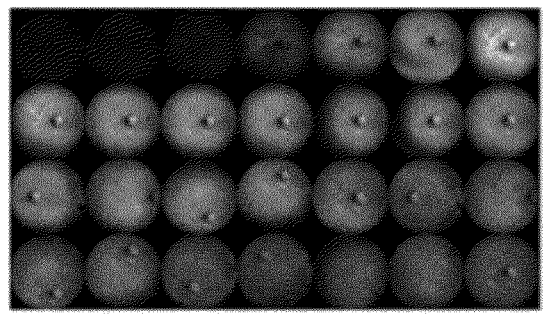
FIGS. 12C to 12F illustrate how modifying the compression parameter ∝ affects the brightness of a sequence of images for different values of ∝.
Figure 12C:
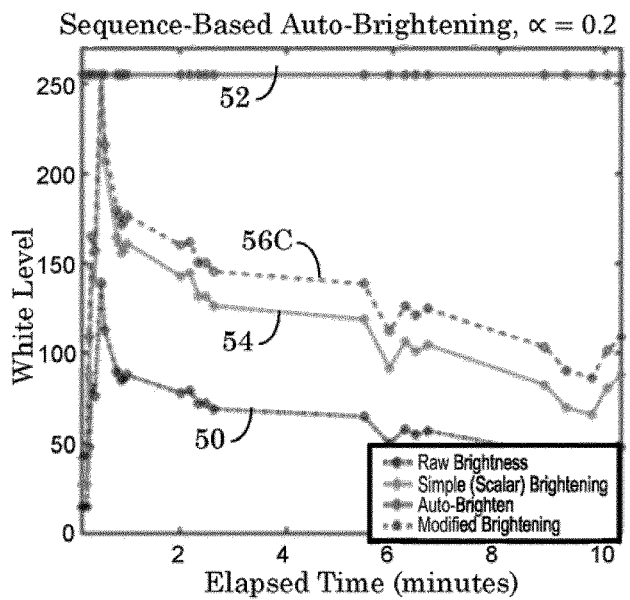
Figure 12D:
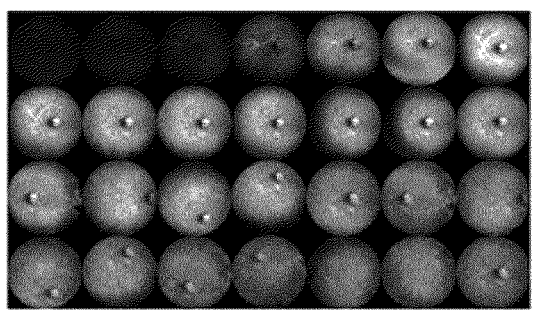
Figure 12D:
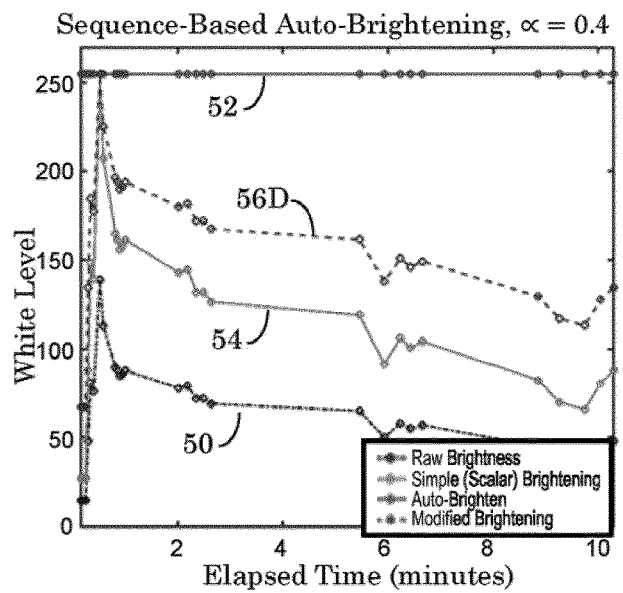
Figure 12E:
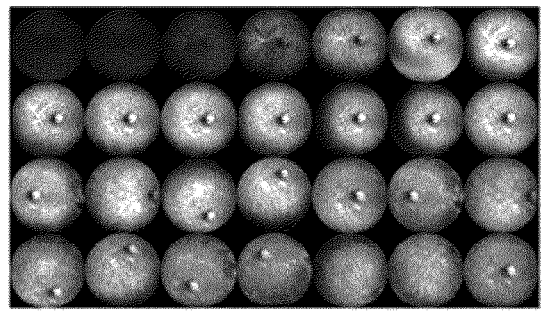
Figure 12E:
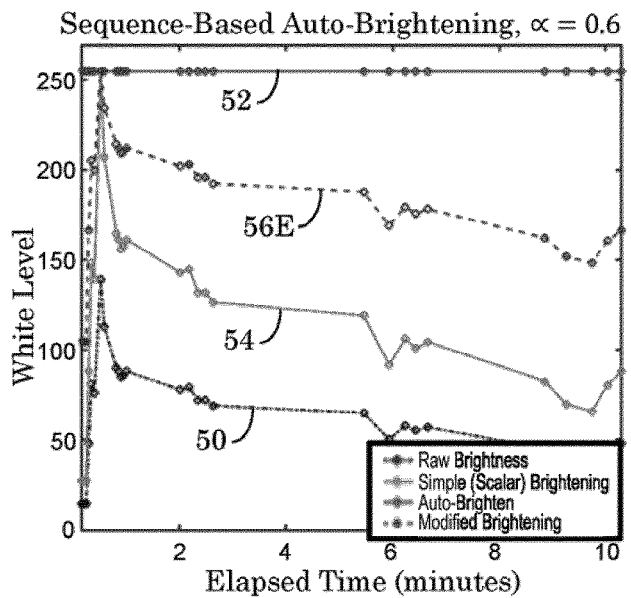
Figure 12F:
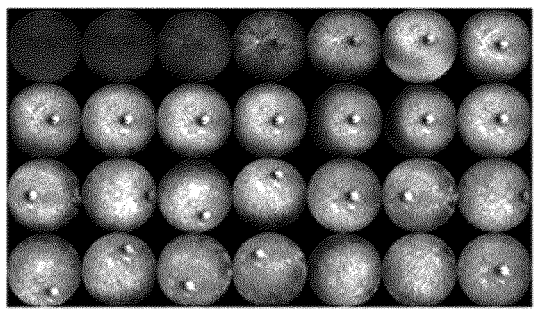
Figure 12F:
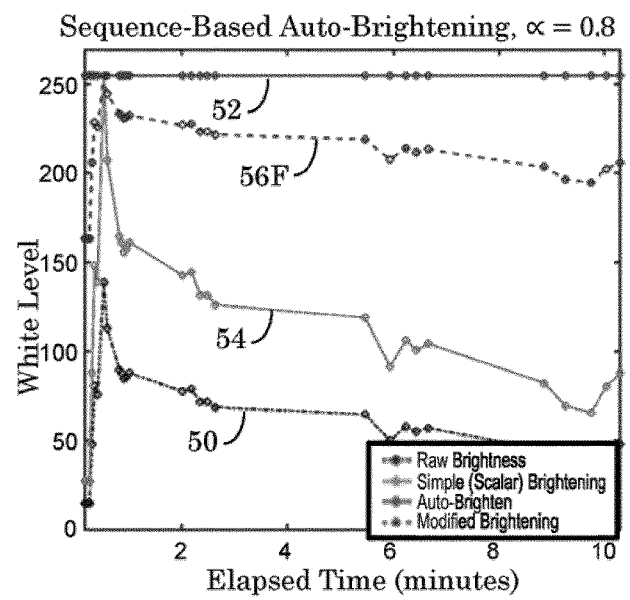

In FIG. 12B, compression parameter $\propto$ is set to one, which is equivalent to auto-brightening each image individually according to its stored white-level, as discussed above in reference to FIG. 9. Again, plot 50 illustrates the relative brightness between raw images, plot 54 illustrates the relative brightness between images using the same brightness factor w max, and plot 52 shows the relative brightness over time between images, each brightened based on their own individual white-level. As is indicated by plot 52, auto brightening each image according to its respective white-level (alone) hides the relative brightness differences between images over time.

FIGS. 12C to 12F illustrate how modifying the compression parameter $\propto$ affects the brightness of a sequence of images for different values of $\propto$. In FIGS. 12C to 12F, compression parameter $\propto$ is increased by increments of 0.2, ranging from $\propto=0.2$ in FIG. 12C to $\propto=0.8$ in FIG. 12F. Each of FIG. 12C to 12F provides a plot of its resultant relative brightness between images (56C to 56F, respectively) in a time-lapse sequence. For comparison purposes, each of FIGS. 12C to 12F show plot 50 (raw images), plot 52 (auto-brightened to their maximum based on their stored white-level), plot 54 (images brightened based on w max). As plots 56C to 56F show, increasing $\propto$ has the effect of increasing the brightness of the displayed sequence of images, as compared to the raw image plot 50, while maintain a similar relative difference between images as raw image plot 50.

Graphical User Interface

Figure 13:
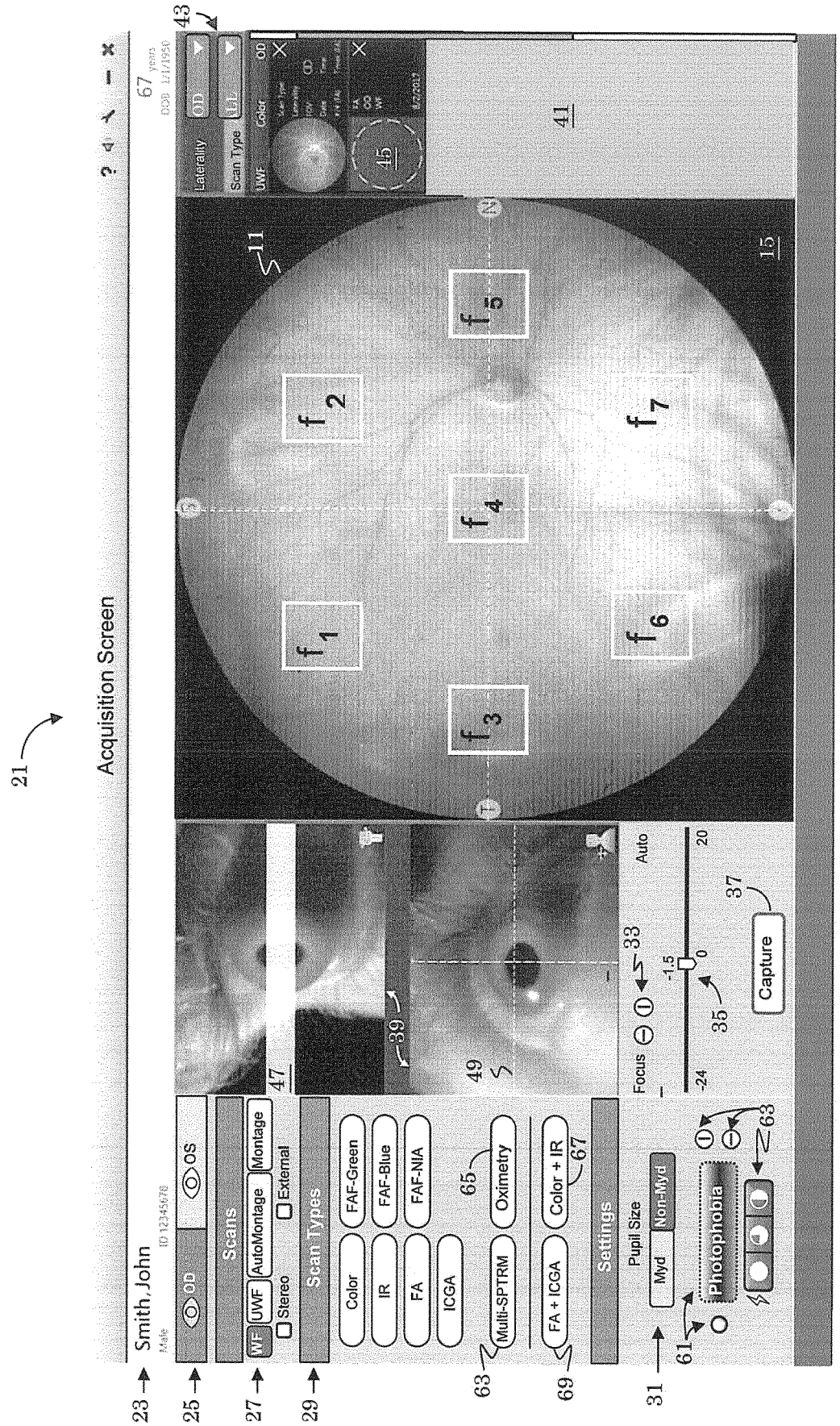
FIG. 13 provides an example of a graphical user interface (GUI) suitable for an ophthalmic imaging device.

As discussed above, the present system provides for expanded focusing functionality. In addition to permitting a user to select among a number of predefined points/regions for focusing, or permitting the user to freely select any random point for focusing, the present invention provides additional features for capturing multiple imaging types (imaging modalities), and/or for modifying specific imaging types to suit a specific patient. By way of illustration, FIG. 13 provides an example of a graphical user interface (GUI) suitable for an ophthalmic imaging device, and which highlights some of these additional features. The GUI provides an acquisition (interface) screen 21 that may be used for acquiring (e.g., capturing) patient images/scans. Optionally, patient data 23 identifying a current patient may be displayed on the top of the acquisition screen 21. The acquisition screen 21 may provide multiple viewports (e.g., framed areas on a display screen for viewing information), display elements and icons to guide an instrument operator through setting acquisition parameters, capturing and reviewing images, and analyzing data. For example, preview window 15 with multiple focus aid locations $f_1$ to $f_7$ overlaid on a preview (fundus) image (e.g., IR preview image) 11 may be provided within a viewport. As is described above, the system operator may select any point (e.g., target focus-region) on preview image 11 for focusing by use of a user-input device (e.g., electronic pointer device, touch screen, etc.).

If desired, additional focus options, such as (step-adjustment) focus buttons 33 or a focus slide bar 35 may be provided. In an exemplary implementation, the target focus-region of preview window 15 and the focus buttons 33, or focus slide bar 35, may be mutually exclusive such that use of one negates the other. For example, use of the focus buttons 33 or focus slide bar 35 may negate any previously, manually selected target focus-region on preview window 15, and apply a traditional, global focus adjustment to the entire fundus image 11 in accordance with the focus buttons 33 and/or focus slide bar 35. Similarly, assigning (e.g. selecting) a target focus-region on review screen 15 may override any focus setting of focus buttons 33 or focus slide bar 35. Alternatively, the target focus-region of preview window 15 and the focus buttons 33 or slide bar 35 may function cooperatively. For example, if a user selects a target focus-region within fundus image 11 on which to focus, the present system may adjust focus at the selected focus-region, accordingly, as is discussed above. If the user, however, wishes to further adjust the focus setting of the selected target focus-region beyond that provide automatically by the present system, the use may use focus buttons 33 and/or slide bar 35 to further adjust the focus at the selected target focus-region. Thus, the present system may provide manual focus for any selected target focus-region within the fundus image 11 (e.g., within preview screen 15).

The acquisition screen 21 may display one or more pupil streams 39 of live images (e.g., infrared images) of the pupil of the eye from different view angles, which may be used to facilitate alignment between the ophthalmic imaging system and the patient. For example, an overlay guide, such as a semi-transparent band 47 or cross-hairs 49, can be superimposed on the live stream(s) to communicate a target location, or target location range, at which the patient's pupil should be positioned for good image acquisition. The overlaid guides inform the system operator regarding a current offset between the target pupil position for imaging, and the current location of the patient's pupil center, so that corrective action may be taken.

Once the operator is satisfied with the capture-settings, an image may be captured by use of a capture-actuating input, e.g., capture button 37.

As images are captured, they may be displayed in thumbnail form in a capture-bin section 41 of the acquisition screen 21. Display filters 43 (e.g. laterality, scan (or image) type, etc.), which may provide a drop down list of filter options, may be used to refine (select or limit) the thumbnails displayed in the capture bin 41. If an imaging mode is selected that requires the acquisition of multiple images (e.g., ultra-wide-field option (UWF), which may montage two captured images, or AutoMontage, which may montages a predefined number of captured images offset from each other), the capture bin 41 may be pre-populated with placeholder icons 45 (e.g. dashed circle) indicating placeholders for the images to be captured. As each required image is captured, the placeholder icons 45 may be replaced with a thumbnail of the captured image to provide the user with an indication of the execution status of the imaging mode.

As it would be understood, however, the system operator may be provided with multiple option settings prior to capturing an image (e.g. actuating a scanning operation). For example, additional display elements and icons may be provided to permit the system operator (the user) to select the types of images (scans) to be acquired and to ensure proper focus and proper alignment of the patient to the ophthalmic imaging system. For example, the laterality of the eye being examined may be displayed/selected, e.g., via laterality icon(s) 25, highlighting which of a right or left eye is being examined/imaged (e.g., the right eye (oculus dexter) OD or the left eye (oculus sinister) OS).

Various user-selectable scan (e.g., imaging) options may be displayed on the acquisition screen 21. The scan options may include FOV buttons 27 for the user to select an imaging FOV of one or more images to be acquired. The FOV option buttons may include a wide-field option (WF) for a standard single image operation, an ultra-wide-field option (UWF) that captures and montages two images, and an "AutoMontage" option that provides a preset montage sequence that collects and montages a predefined number (e.g., four) of images, and/or a user-definable "Montage" option that permits the user to submit a user-specified montage sequence. In addition, checkboxes may be provided to indicate whether a user wishes to perform stereo imaging and/or use an external fixation target. Selecting the external fixation target, may disable the internal fixation target in the system during imaging.

A fundus imaging system may support multiple scan types (e.g., imaging modalities). Examples of scan types may include color imaging, which provides a view of the fundus in full color, but which requires a bright light that a patient may find discomforting. Another type of images are IR images, which are invisible to a patient and thus more comfortable. IR images are generally monochrome image, and can be helpful in identifying more detail than color images. Some types of tissues have natural light-sensing molecules that can be made to fluoresce at certain wavelengths, e.g., 500 to 800 nm, and these tissues may be used to identify potential regions/structures of pathology that might not be easily defined in color or IR frequencies. Imaging the eye using a specific wavelengths selected to cause a target-type of tissue to fluoresce is termed fundus autofluorescence imaging (FAF). FAF imaging at different frequencies may cause different types of tissue to autofluoresce, and thereby provide a different diagnostic tool for a different type of pathology. Other imaging modalities include FA and ICGA, which as is explained above, make use of an injected dye to follow blood flow in a series of images.

In the present example, acquisition screen 21 provides a scan type section 29 to select among multiple imaging modalities. Examples of selectable scan types may include:

Color (e.g., true color imaging using visible light, such as red, green, and blue light components/channels); IR (imaging using non-visible infrared light, e.g., by use of an IR laser); FAF-Green (fundus autofluorescence with green excitation), and FAF-Blue (fundus autofluorescence with blue excitation); FAF-NIA (fundus autofluorescence using near infrared light); FA (fluorescein angiography, e.g., by injecting fluorescein dye into the patient's bloodstream); FA-NIA (fluorescein angiography using near infrared light); and ICGA (indocyanine green angiography, e.g., by injecting indocyanine green dye into the patient's bloodstream).

Acquisition screen 21 may further provide inputs for various image capture settings, such for a dilated eye (mydriatic mode), a non-dilated (non-mydriatic) eye, and/or an eye that may have light sensitivity (e.g., a patient that suffers from photophobia). The user may select between mydriatic (Myd) and non-mydriatic (Non-Myd) imaging modes by selecting a button 31 for the respective mode. Optionally, the system may automatically choose (e.g., auto-select) which mode is appropriate based on conditions of the eye.

The operator may make use of multiple photophobia-related settings prior to initiating an image capture sequence. Optionally, the system may identify/flag a patient as having been previously diagnosed as suffering from photophobia, or as being a candidate for being sensitive to light. In ether, case, the system may alert the operator to the fact and suggest that the imaging sequence be adjusted accordingly. For example, if a patient is a candidate for light sensitively, a warning icon/button 61 may be lit, change color, and/or flash to draw the operator's attention. The operator may then select a default photopia setting by selecting the button and/or manually selecting from a list of light-intensity modifying options 63, each of which may adjust an applied light intensity during image acquisition. Tuning (adjusting) the image acquisition settings in accordance with a patient's medical condition (e.g., photophobia) is an example of patient tuned diagnostics.

Patient Tuned Diagnostics

Ophthalmic imaging systems may use flashes of light, such as in a scanning pattern, to acquire fundus images. For example, the CLARUS500™ from Carl Zeiss Meditec Inc. may use flashes of light to capture high resolution wide field images. Some types of light flashes, such as those used for FAF-Blue mode imaging, can be bright and have short term vision impacts on a patient including spotty, diminished, and/or color reduced vision. For patients experiencing photophobia, e.g., discomfort or pain to the eye due to light exposure, the light source of an ophthalmic imaging system can be significantly more impactful and trigger short term effects including pain, migraines, nausea, watering eyes, and other conditions.

Typically, when imaging a patient with known light sensitivity, a system operator may take steps to reduce the amount of light exposure to the patient. For example, the system operator may run diagnostics on (e.g. image the eye of) patients with light sensitivity by avoiding dilation of the patient's eye and conducting testing (e.g. imaging) in a dark room setting. If possible, the system operator may attempt to reduce the light intensity of the system and use a smaller FOV imaging, but this can result in reduced image quality.

Herein is presented an ophthalmic imaging system having a diagnostic mode (e.g. an imaging mode) for patients who have light sensitivity and/or a system capable of identifying patients who may be candidates for light sensitivity.

Figures 14, 15:
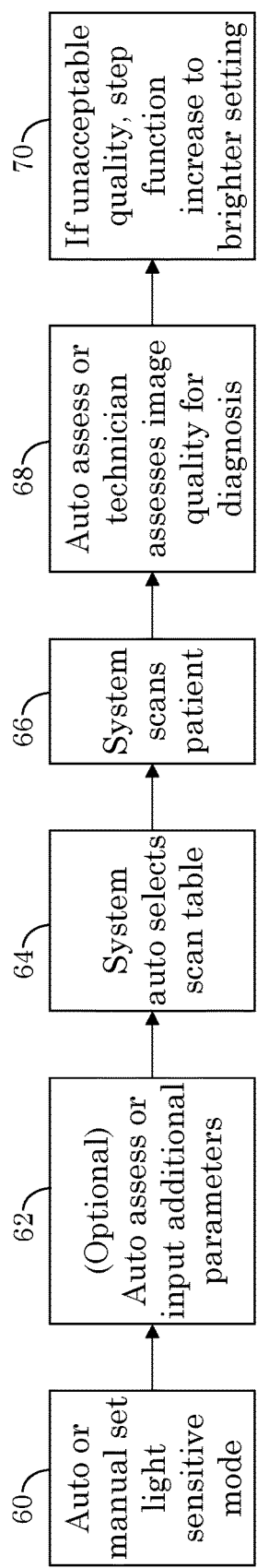
FIG. 14 provides an example process for tuning (e.g., adjusting) the amount of light reduction according to the relative light sensitivity of a patient.
FIG. 15 illustrates how a scan table (e.g., intensity level used for image acquisition) may be selected and/or may be modified based on pupil size and/or iris color.

The present system may provide an imaging mode (e.g., a photophobia mode or light sensitive mode) 'tuned' for light sensitive patients that reduces the light output of the ophthalmic imaging system, but delivers a (e.g., minimally) viable image quality for diagnosis. FIG. 14 provides an example process for tuning (e.g., adjusting) the amount of light reduction according to the relative light sensitivity of a patient. This may include an optional automated mode for patients identified (e.g., in their medical record) as being light sensitive and providing a system operator with a manual selection/de-selection option within a graphical user interface (GUI), such as within an image acquisition screen (e.g., button 61 and/or 63 in FIG. 13). Thus, the process may begin by setting the light sensitive mode, automatically or manually, step 60, such as by checking patient records. Optionally, the assessment of the level of the patient's light-sensitivity may be adjusted/determined by providing additional information/parameter (step 62), such as iris size, iris color, and/or light/dark retina detection.

A scanning-based ophthalmic imaging system may use a scan table that specifies the light frequency, intensity, and/or duration of a scan line applied at a given position on the fundus. Typically, one scan table would be constructed/defined per imaging type. Implementation of the present photophobia mode, however, may include generating one or more scan tables using a fraction of the current/standard light setting (e.g. the default light setting) for a given imaging type. The scan tables may provide for both reduced light intensity and reduced duration (e.g., shorter-timed flashes). The scan tables may also include unique scan settings (e.g., additional intensity and duration adjustments) based on the patient's pupil size and/or iris color. Minimally viable image quality based on minimal light exposure in each imaging mode/type (Color, FAF-B, FAF-G, IGC, FA) may be predetermined based on clinical testing. For example, patients with light sensitivity may be examined (imaged) using the light sensitive mode first by letting the system may automatically select one of the alternate scan tables based on the amount of light sensitivity of the patient (step 64). Alternatively, the user may select a predefined alternate scan table. The system then scans (images) the patient using the selected scan table (step 66), and an assessment of the acquired image is then made (step 68). This assessment may be automatically made by the system, such as by determining an image quality measure of the acquired image, or be made by the system operator. If the resultant image(s) are not of sufficient quality, additionally images may be taken with step function increase in intensity up to a normal mode intensity, if required, step 70. Manual selection of this step increase may be made, for example, by use of inputs 63 in FIG. 13.

The present system may include optional elements/parameters (e.g., as indicated by optional step 62) such as auto detection of pupil size, iris color, automated light/dark retina detection (e.g., using an IR preview image of the retina). Lightly colored retinas are prone to be more photophobic than darkly colored retinas. A direct table correlation may be made between different combination of photophobic indicators and a corresponding light/duration setting (e.g., scan table selection) for a given image acquisition operation. Alternatively, a mathematical equation may be created for optimal (minimal) power setting based on the combination of image quality affecting parameters. Additionally, the present system may further integrate DNA data to automatically adjust the diagnostic device settings based on a marker or a collection of markers that may be indicative of possible light sensitivity. This can further be extended to mathematical evaluation of marker sets for optimal setting.

FIG. 15 illustrates how the scan table (e.g., intensity level used for image acquisition) may be selected and/or may be modified based on pupil size and/or iris color. Optionally, the default intensity and duration settings of the system may be set to minimal settings associated with light eyes, and the intensity (and/or duration) may be increased for less photophobic eyes. Further optionally, the default intensity and duration settings of the system may be set to minimal settings associated with light eyes, and if the captured image quality is not greater than a minimum value, the intensity and/or duration may be automatically increased in predefined step increments to capture additional images within a current image capture sequence until images of minimum quality are achieved.

The present patient tuned diagnostics may augment an existing ophthalmic imaging system with multiple operating modes based on known patient conditions or diseases, such as adding a dry eye mode for OCT imaging. The present approach may also be applied to patients with mental health conditions wherein discomfort, such as stress or anxiety, may be triggered by light flashes or bright intensity. For example, the present patient tuned diagnostics may be applied to patients with post-traumatic stress disorder, PTSD, to minimize patient discomfort and adverse conditions.

Figure 16:
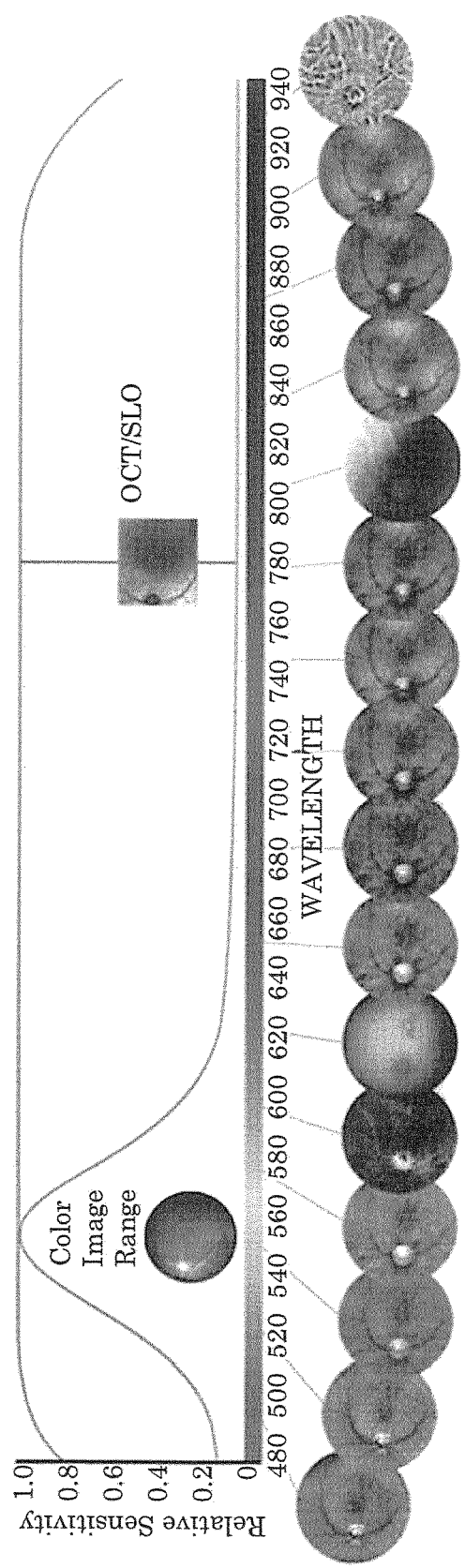
FIG. 16 illustrates an example series of multiple images across multiple wavelengths that may be taken in response to a single capture command input with the multi-spectrum option selected.

Returning to FIG. 13, as is indicated by scan type section 29, the present system may further provide for functions for acquiring multiple image types (different imaging modalities) with one button. As is explained more fully below, this may be achieved by providing a scan table that supports multiple imaging modalities within a single image capture sequence. For example, a multi-spectrum option/button 63 may be provided for capturing multiple images across a spectrum of wavelengths. FIG. 16 illustrates an example series of multiple images across multiple wavelengths that may be taken in response to a single capture command input with the multi-spectrum option 63 selected. Another example may be an oximetry option/button 65 that determines a measure of oxygen in blood by capturing multiple images at different select wavelengths, as is explained more fully below. Also provided is a Color+IR option/button 67, which captures both a color image and an IR image within a single image capture sequence in response to a single image capture button. Another option may be an FA+ICGA option/button 69 for taking both an FA and an ICGA image, or sequence of images, in response to a single image capture command. A preferred method for implementing the FA+ICGA option is provided herein.

Sequential Acquisition of FA and ICGA Images in Response to a Single "Capture" Command Both Fluorescein Angiography (FA) and Indo-Cyanine Green Angiography (ICGA) can be performed as part of a single exam. ICG (Indo-Cyanine Green) dye can be injected immediately before or after the fluorescein, or a mixed bolus may be used. FA images may be acquired using a blue/green illumination source, and ICGA images are acquired using a near-infrared illumination source. Combining both modalities into a single exam shortens the patient chair time. However, acquiring sufficient numbers of both FA and ICGA captures throughout the different phases of the angiogram may be burdensome both for the patient (particularly for those who are more photophobic) and the operator. This burden can be reduced by using an imaging device that is capable of acquiring both an FA and an ICGA image within a single exposure sequence.

Acquiring both FA and ICGA images simultaneously presents a challenge for the system design, because of the different light sources and optical filter requirements for the respective modalities. Because of the risk of eye motion, the exposure needs to be completed in a short amount of time (~100 ms), while still achieving sufficient image quality for a doctor to assess the condition of the eye.

With any instrument that delivers visible light to the retina, patient comfort is an important consideration in ensuring compliance; patients experiencing photophobia may move or blink excessively during imaging, and may even refuse to complete the examination. As is explained in "Action spectrum for photophobia," by J. M. Stringham et al., JOSA A, 2003, 20(10), 1852-1858, photophobia sensitivity increases with decreasing wavelength. The short wavelengths of light typically used for FA (470-510 nm) are far more uncomfortable than the near-infrared light used for ICGA. It has further been shown that perceived flash duration increases as a function of flash duration (Osaka, N., "Perceived brightness as a function of flash duration in the peripheral visual field," Perception & Psychophysics, 1977, Vol. 22 (1), 63-69). Therefore, to aid patient comfort, it is desirable to minimize the duration of potentially painful light exposures (as well as minimizing the flash energy).

Figure 17:
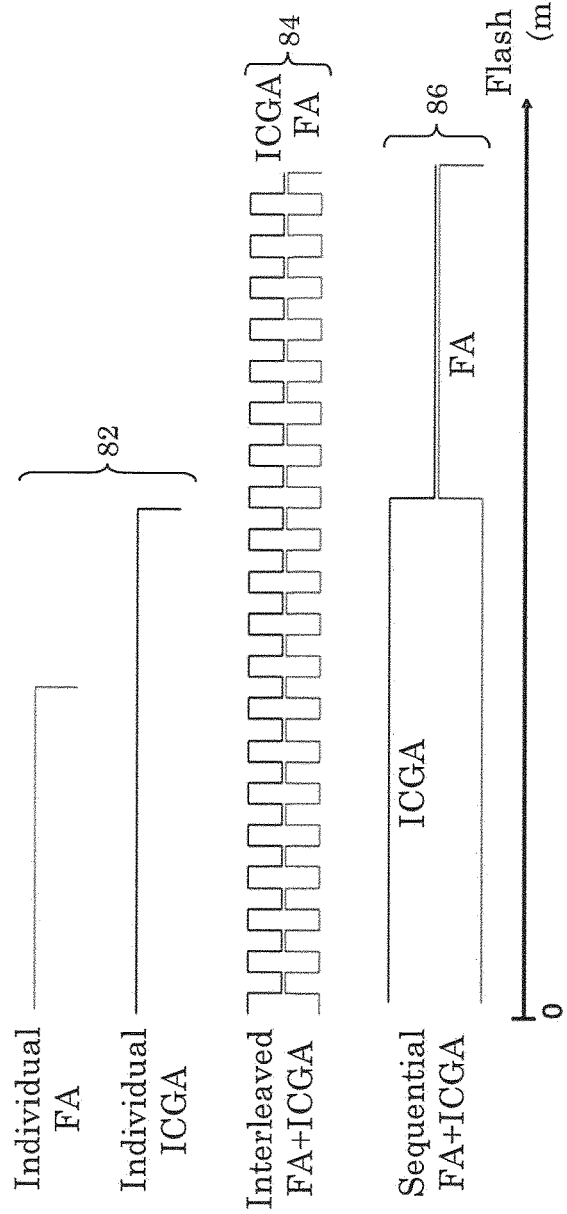
FIG. 17 compares the present invention with two previous methods of providing FA+ICGA functionality in response to a single capture command.

FIG. 17 compares the present invention with two previous methods of providing FA+ICGA functionality in response to a single capture command. A first previous approach 82 uses both blue and infrared laser sources to deliver light to the eye at the same time, and collecting the emitted fluorescent light simultaneously by use of two separate photodetectors. A second previous approach 84 interleaves (or alternates) the illumination and detection: the laser sources are alternated such that one line of the FA image is scanned, then one line of the ICGA, then a second line of the FA, and so on. These two approaches have the advantage that the acquired FA and ICGA images will be precisely co-registered, even in the presence of eye motion. This may have benefits for image post-processing and visualization tools.

These two prior approaches, however, also have their disadvantages. The truly simultaneous approach 82 requires relatively complex hardware, e.g., separate detectors and filters are required for each of the FA and ICGA collection paths. The interleaved approach 84 may have a disadvantage in terms of patient comfort, because the blue/green FA illumination source (which is far more bothersome for patients than the ICGA source) is perceived by the patient to be persistent through the full duration of the exposure (i.e., a long flash). This may provoke a photophobic reaction (e.g., blinks, pupil constriction, eye motion, and Bell's phenomenon).

The presently preferred approach 86 captures an FA and an ICGA image sequentially, in response to a single "capture" command from the user. That is, within a single image capture sequence (e.g. within a single flash time), a full ICGA image (or image sequence) is captured immediately followed by capturing a full FA image (or image sequence).

In a preferred embodiment, the ICGA image is scanned first, because the required infrared source is not uncomfortable for the patient. When the ICGA image acquisition scan is complete, the FA scan is then initiated. This differs from the two previous approaches for simultaneous FA+ICGA captures, which either illuminate the eye with both light sources at once (82), or interleave multiple FA and ICGA acquisitions to build up images of both (84).

Because the present, sequential FA+ICGA approach 86 reduces the time interval of perceivable visible light exposure (as compared to interleaved FA+ICGA approach 84), it may provoke less patient photophobic discomfort and reduce the probability of blinks and/or eye motion artifacts. That is, the time between when the visible light (e.g., for FA) begins until when it ends is much shorter than for an interleaved flash that delivers the same energy, and therefore the interval during which photophobia may be induced in the patient is minimized. This may lead to improved patient comfort and image quality from the angiography exam. The present approach 86 also avoids the complex hardware requirements of the first approach 82. Indeed, the present approach 86 may be implemented by use of an appropriate defined scan table.

In addition to the present FA+ICGA, the present system may provide additional multi-spectral fundus imaging modes 63-67, as shown in reference to FIG. 13.

Single-Capture Multi-Spectral Imaging for Slit-Scanning Ophthalmoscopes

Multi-spectral fundus imaging can provide enhanced visibility and discrimination of retinal structure and function by consolidating information obtained from images acquired with multiple wavebands of light (e.g., visible and non-visible reflectance and autofluorescence).

True-color fundus imaging is standard in retinal examination. Near-infrared light can penetrate deeper into the retina, as the longer wavelengths are less prone to absorption by blood and melanin. Thus, infrared fundus imaging can sometimes provide complimentary information to true-color imaging, by enabling better visibility of sub-retinal features (such as small drusen beneath the RPE).

Blood oxygenation can be non-invasively probed in the retina using a multi-spectral imaging approach. As is explained in "Oximetry of retinal vessels by dual-wavelength imaging: calibration and influence of pigmentation," by J. M. Beach et al., Journal of Applied Physiology, 86, no. 2 (1999): 748-758, two or more excitation wavelengths (one for which blood absorption is insensitive to oxygenation) may be used to capture reflectance images, which can be used to infer blood oxygen saturation, given suitable calibration for vessel caliber and retinal pigmentation.

In fundus autofluorescence (FAF) imaging, the acquired image information differs depending on the spectral content of the excitation and collection wavebands. These differences can be used to extract clinical information on the condition of the retina. Collecting FAF over separate wavebands can, for example, be used to distinguish fluorophores in the retina, such as is described in "Color Autofluorescence Imaging in Age-Related Macular Degeneration and Diabetic Retinopathy," by M. Hammer, Investigative Ophthalmology & Visual Science, 49, no. 13 (2008): 4207-4207. Similarly, varying the FAF excitation waveband can be used to estimate the optical density of the macular pigment, as is described in "Macular pigment density measured by autofluorescence spectrometry: comparison with reflectometry and heterochromatic flicker photometry," by Delori, Francois C. et al., JOSA A, 18, no. 6 (2001): 1212-1230.

All references mentioned herein are incorporated by reference in their entirety.

In most commercial fundus imaging systems, acquiring multi-spectral data typically requires multiple captures, which is time-consuming for the operator and uncomfortable for the patient. The present system provides paths to extend widefield slit-scan fundus imaging to deliver multi-spectral fundus imaging, using only single-capture protocols.

Some prior fundus imaging systems provide imaging at multiple wavelengths, but these are typically offered as individual scan modes, with each mode requiring a dedicated capture input. Thus, for example, to acquire both RGB color and infrared images, two separate scans are needed, and the resulting images are likely not registered (due to unavoidable eye motion/re-alignment between scans). A prior approach to oximetry employs a simultaneous two-wavelength method for oximetry. The color sensor's Bayer filter is used to separate the wavelength channels, and analysis software provides calculations of vessel hemoglobin oxygen saturation. Academic studies have used prior systems that employ two separate FAF imaging modalities for macular pigment assessment. The CLARUS™ 500 also offers two different FAF excitation/detection bands. Each mode, however, requires separate dedicated captures.

Herein is presented a technique for simultaneous color-plus-infrared Imaging.

Figure 18:
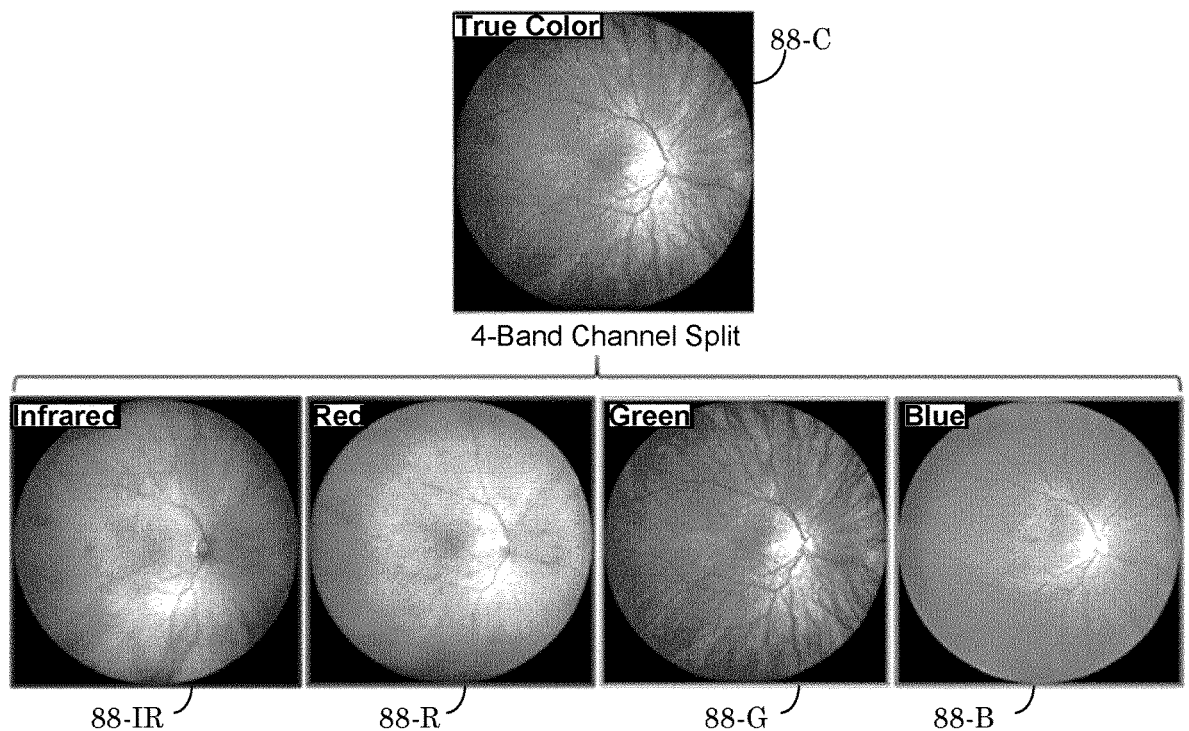
FIG. 18 shows a color fundus image comprised of four channels.

In one application, sequenced multi-spectral scanning removes the need to acquire IR images as an additional scan. Instead, a perfectly-registered IR image is automatically provided with every true-color scan. The additional image information may be made available to the user through a 4-band channel-split feature in a review screen of the instrument software. For example, FIG. 18 shows a color (e.g., true color) fundus image 88-C comprised of four channels. That is, in addition to the typical red channel 88-R, green channel 88-G, and blue channel 88-B, the present color image 88-C additionally has an infrared channel 88-IR.

The present ophthalmic imaging system images the retina using sequenced light sources and a monochrome camera. This is achieved using scan tables that for each slit acquisition instruct the hardware to switch on a particular light source. This method affords great flexibility, both in terms of scanning and sequencing of different types of light.

The ordering of scan table commands is used to group the acquired slit images by individual color so that they can be assembled into separate images, which are then combined together in processing to form a true-color image. A scan table may be arranged in rows and tables of parameters used by the system to identify a specific scan location, excitation wavelength (e.g., channel), etc. For example, in a typical scan table for a true-color mode, each row in the table commands a slit acquisition, and a 'channel' column tracks the light-color for that particular acquisition, which is later used to assemble the image color channels separately. In this case, the channels may be R, G, and B to denote the red, green, and blue color LED acquisitions. To expand the capture of a color image to include the capture of an IR image, the scan table may be modified to incorporate additional IR acquisitions (which would be denoted 'I' in the 'channel' column of the scan table), such that each sequence of R, G, and B in the 'channel' column for a color image would extend to a sequence of R, G, B, and I. This would effectively provide a 4-channel multispectral image. Thus, every true-color image would also provide a perfectly-registered IR image as an integral part of the scan. It is noted that IR light is not uncomfortable for patients, and so does not significantly impact flash brightness. For FAF with multiple excitations, green and blue illuminations would be similarly sequenced in a scan table, with a long-pass barrier filter (e.g., >650 nm used for collecting the remitted FAF signal).

Figure 19:
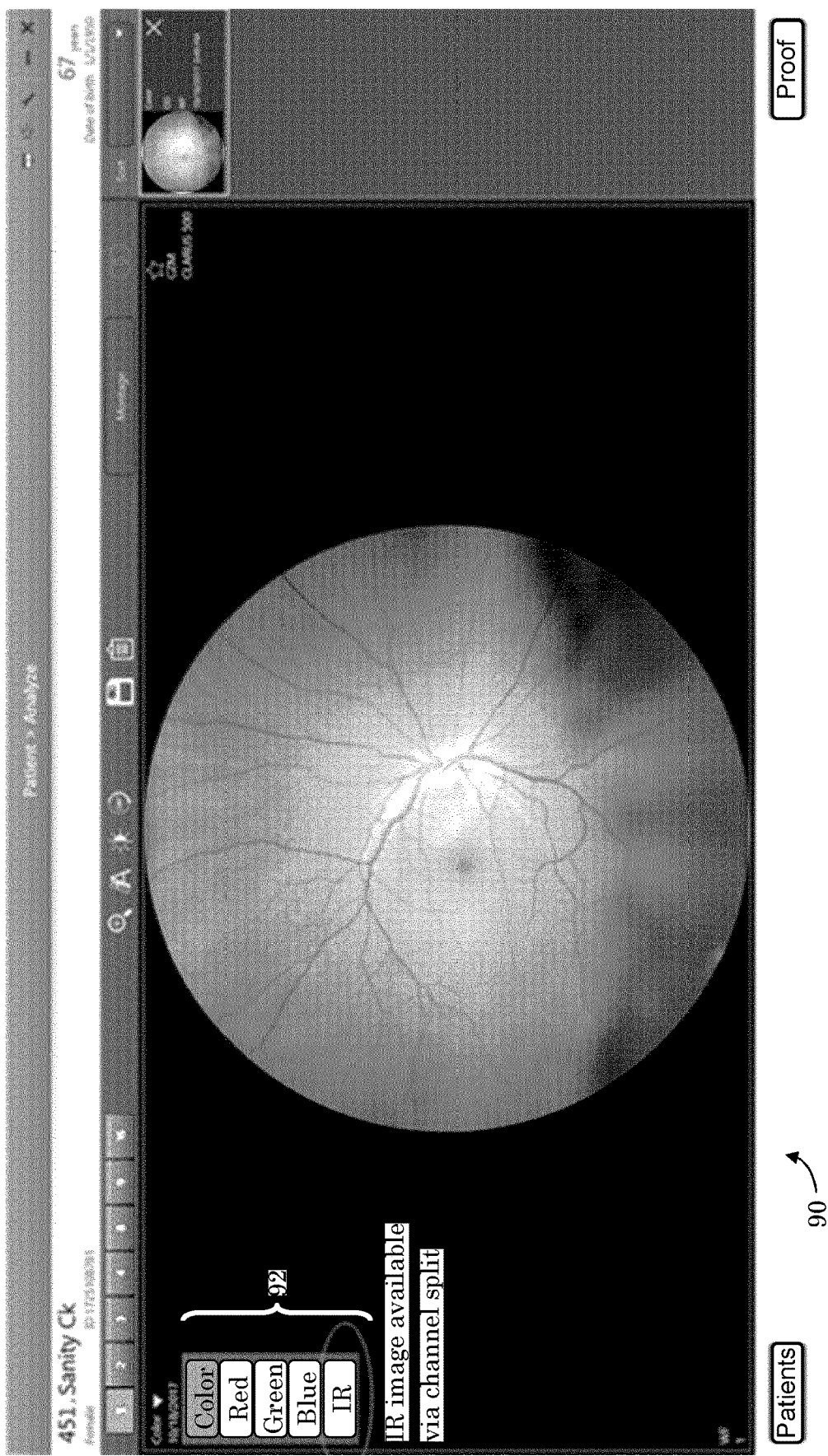
FIG. 19 show an example of a "channel-split" review screen that provides an option for viewing the red, green, blue, and infrared channels in isolation.

Because all color channel component images are acquired in a single flash sequence, they would be perfectly registered (barring any eye motion during the scan). Choice of each channel view could be provided in a "channel-split" review screen. For example, FIG. 19 show an example of a "channel-split" review screen 90 that provides an option 92 for use by a system operator that allows the operator to view the red, green, blue, and infrared channels in isolation. In another embodiment, the IR image information could be combined with the color image to form a composite image. For example, the red channel of the color image could be linearly combined with the IR image information, to provide a "depth-enhanced" true-color fundus image.

Unlike previous systems that provide IR imaging as a distinct capture mode, the present technique may provide an IR image automatically as part of every true-color capture. This has the advantages that no additional chair-time is required, there is no discernible added discomfort for the patient, and the resulting IR image is perfectly registered to the color image. The feature might serve to increase interest in IR imaging among retina specialists, as the additional information given by IR would be provided to them at no discernible cost.

Herein is also presented a technique for oximetry of retinal blood vessels. Blood oxygen saturation can be non-invasively probed in the retina using a multi-spectral reflectance imaging method. In a basic approach, just two excitation wavelengths are required. One excitation wavelength is chosen such that its absorption by hemoglobin (to which blood oxygen binds) is independent of the level of oxygen saturation (isosbestic). The other excitation wavelength should exhibit significant difference in absorption between oxy- and deoxy-hemoglobin.

Figure 20:
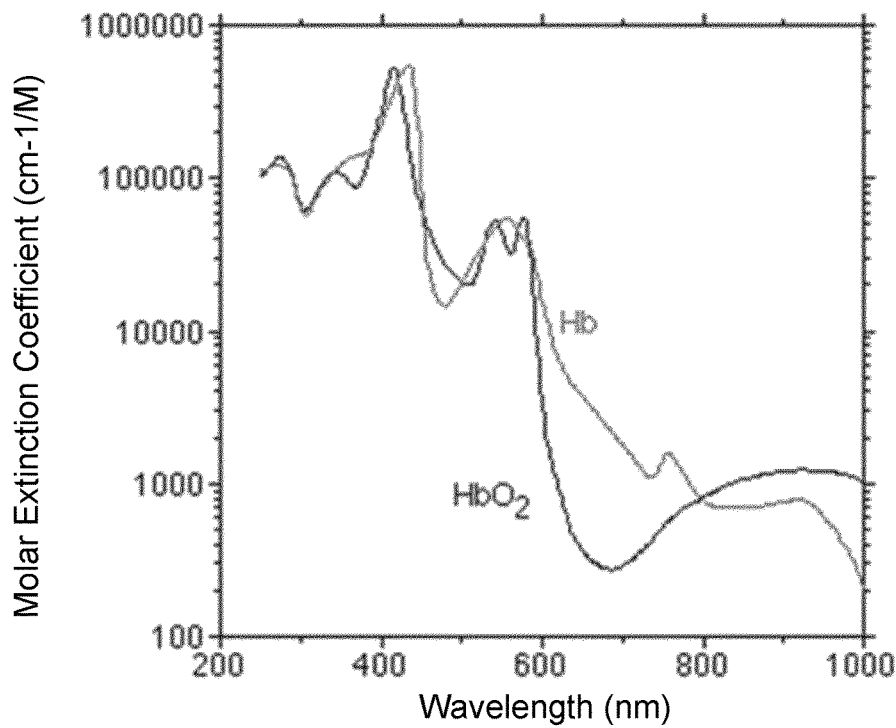
FIG. 20 shows the oxygenated and deoxygenation hemoglobin extinction spectra.

FIG. 20 shows the oxygenated and deoxygenation hemoglobin extinction spectra. Suitable isosbestic points are found at 390, 422, 452, 500, 530, 545, 570, 584, and 797 nm. The employed wavelengths should be as close as possible, to minimize wavelength-dependent differences in light transport within the retina (e.g., scattering). The presently preferred approach for oximetry provides a wide field-of-view, and uses the slit-scanning technique, as well as sequenced illumination (rather than, e.g., the Bayer filter separation used by prior methods).

Figure 21:
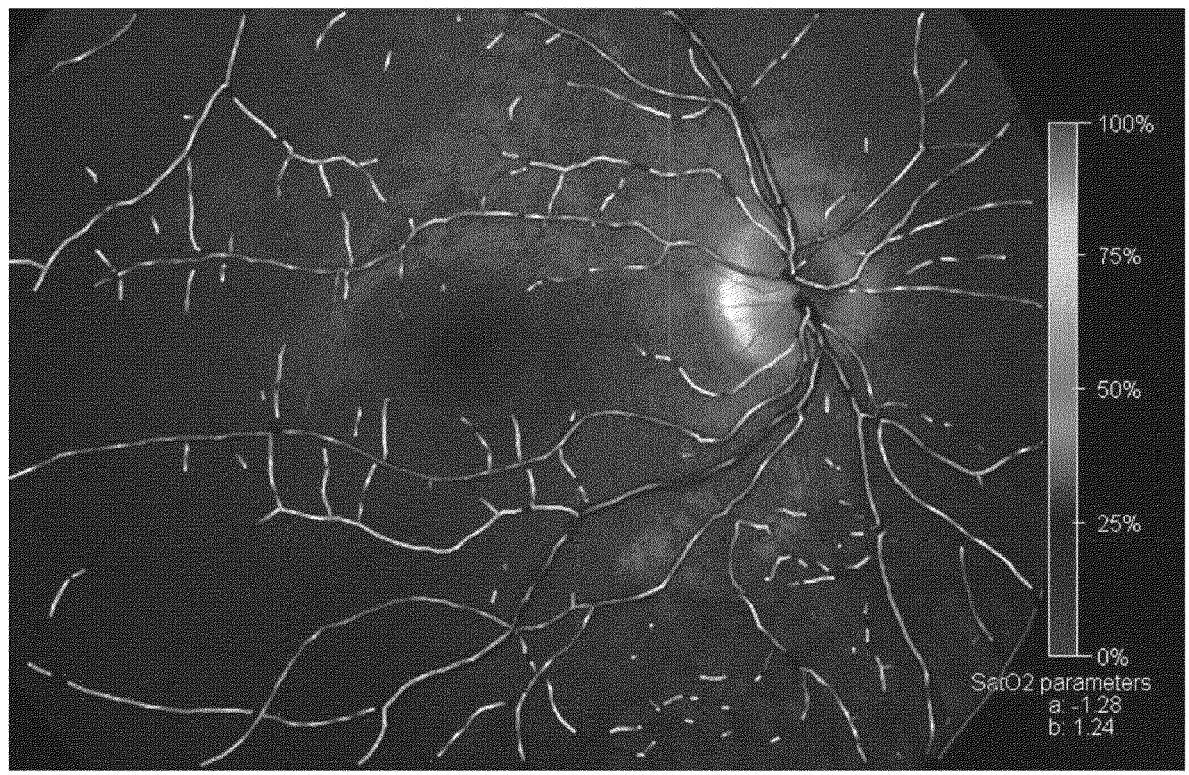
FIG. 21 provides an example of an oxygen saturation map.

The present system may achieve oximetry by use of a dedicated excitation filter in a slit wheel. The filter may be a dual-bandpass or stacked filter, with 5-10 nm notches to pass light at two wavelengths. The wavelength notch centers may be chosen such that they are suitable for two-wavelength oximetry and can be provided by separate LEDs in a lightbox (for example, 570 nm and 615 nm). The method for performing oximetry may then be as follows:

a) Sequence green and red light in a single scan pattern, thus collecting the two 570 nm and 615 nm images in a single capture (no need to register them).
b) Segment the blood vessels.
c) Apply the method employed by Beach et al. [1] (with some calibration for vessel diameter and variation in retina pigmentation).
d) Display an oxygen saturation map. FIG. 21 provides an example of an oxygen saturation map.

The present system may further be used to measure the macular pigment optical density. In this case, autofluorescence images with dual-wavelength excitation are obtained in a single scan, by sequencing blue and green excitation. The acquired data allows for an objective measurement of the macular pigment optical density (MPOD). The MPOD is potentially clinically useful in determining a patient's risk of developing age-related macular degeneration (AMD). AMD is the leading cause of blindness in the western world. It is a progressive and incurable disease which impacts the macular area of the retina, resulting in a loss of central, high resolution color vision. The disease primarily affects people over 50 years of age. Incidence is generally higher in Western countries due to older age profiles, dietary habits, and lighter on-average eye pigmentation. Measurement of MPOD could offer some advantages to doctors, particularly in a screening setting. MPOD measurement would open possibilities for health providers to provide dietary supplements (of which there are many on the market), and to extend their purview into the dietary health of patients. The presently preferred method may use a sequenced FAF capture using multiple excitation bands to enable an objective measurement of macular pigment optical density, using a single image capture.

In a preferred embodiment, autofluorescence images with dual-wavelength excitation are obtained in a single scan, by sequencing blue and green excitation with the >650 nm barrier filter normally used for FAF-Green. Non-mydriatic mode can be used, to allow for small-pupil imaging in an OD screening setting, and patient comfort in response to the flash could be optimized by restricting the scan to the macula and surrounding region. The acquired data should allow for an objective measurement of the macular pigment optical density.

Figure 22:
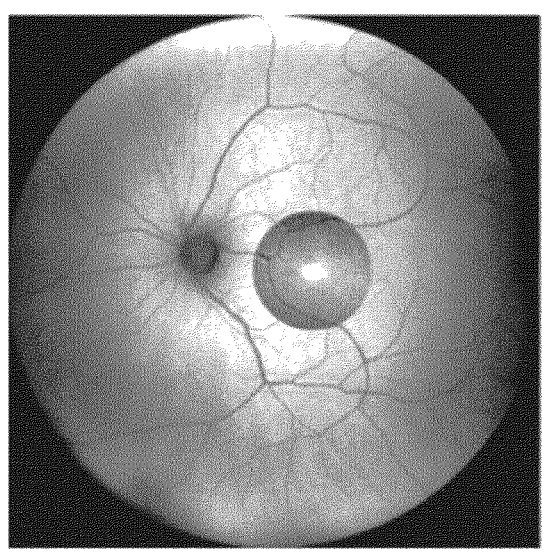
FIG. 22 illustrates the principle of the MPOD measurement (left) and MPOD profile (right).
Figure 22:
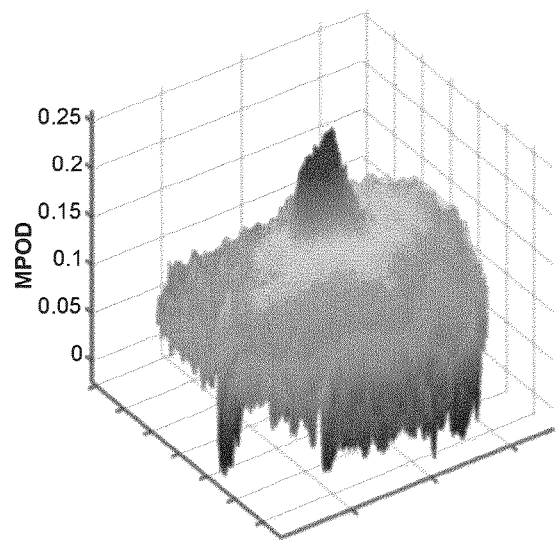

FIG. 22 illustrates the principle of the MPOD measurement (left) and MPOD profile (right). FAF-Green image with overlay (in a predefined color, e.g., yellow) of normalized difference between FAF-Green and FAF-Blue. This normalized difference can be used to infer an MPOD profile.

Herein are provided some consideration for multi-spectral imaging. Additional light sources of various wavelengths could be incorporate into the lightbox design for single-exposure, sequenced, multispectral imaging. This could provide for multispectral imaging feature with a single exposure (rather than many) and with perfectly-registered image output.

Figure 23:
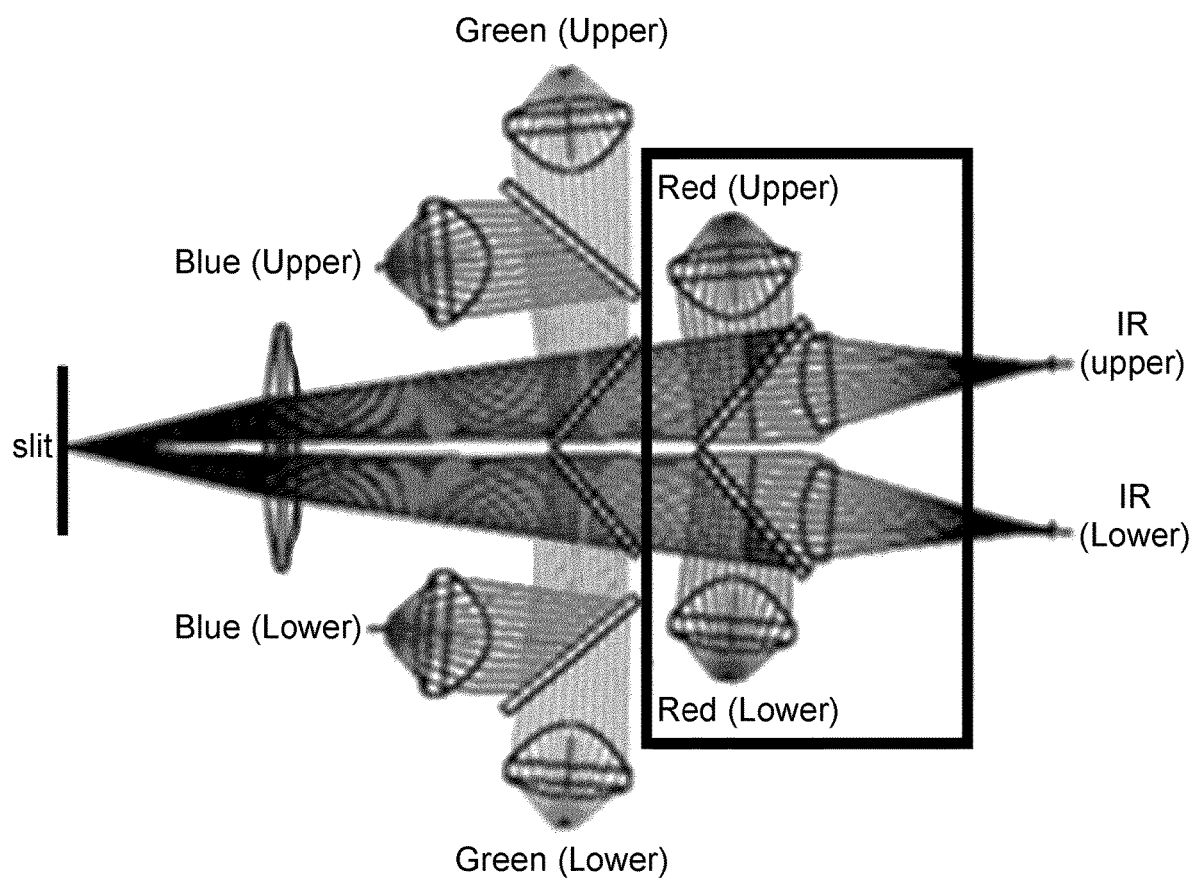
FIG. 23 illustrates a lightbox design with 8 light sources (2 each of red, green, blue, and IR).

FIG. 23 illustrates a lightbox design with 8 light sources (2 each of red, green, blue, and IR). Typically, only one of each source is necessary for imaging in non-mydriatic mode, though there is some benefit to using both sources of each color when possible on larger pupils (to obtain better image SNR (signal-to-noise ratio) and suppress reflexes more effectively). However, the light-box design may be modified to incorporate additional sources. This could provide for the multi-spectrum function 63 of FIG. 13, which offers imaging, using multiple combinations of LED (light-emitting diode) sources and filters, at wavelengths across the 500-940 nm range, as illustrated in FIG. 16.

Returning to FIG. 13, multiple multi-function (combination) keys 63-69 are provided that take more than one type of image in response to a single control input from a system operator. These combinations are predefined and presented as fixed multi-function keys 63-69, but optionally, an operator may define custom multi-function keys that capture multiple images of different imaging modalities in response to a single capture command. For example, the operator may be provided with a set-up window to link additional types of images to a single image type-choice. It is noted that different types of images may require different types of filters, and if a system only supports the use of one filter at a time, then this may limit the number of types of images that may be linked together (e.g., only image types that require a similar filter may be linked together). The system my limit the available choices accordingly. Alternatively, if the system has multiple detectors, each with its own filter, then a light splitter may be used to divert light of different wavebands to the different detectors via their respective filters. This would increase the number of types of images that may be linked and taken in response to single capture command.

Hereinafter is provided a description of various hardware and architectures suitable for the present invention.

Fundus Imaging System

Two categories of imaging systems used to image the fundus are flood illumination imaging systems (or flood illumination imagers) and scan illumination imaging systems (or scan imagers). Flood illumination imagers flood with light an entire field of view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera. A scan imager provides a scan beam that is scanned across a subject, e.g., an eye, and the scan beam is imaged at different scan positions as it is scanned across the subject creating a series of image-segments that may be reconstructed, e.g., montaged, to create a composite image of the desired FOV. The scan beam could be a point, a line, or a two dimensional area such a slit or broad line.

Figure 24:
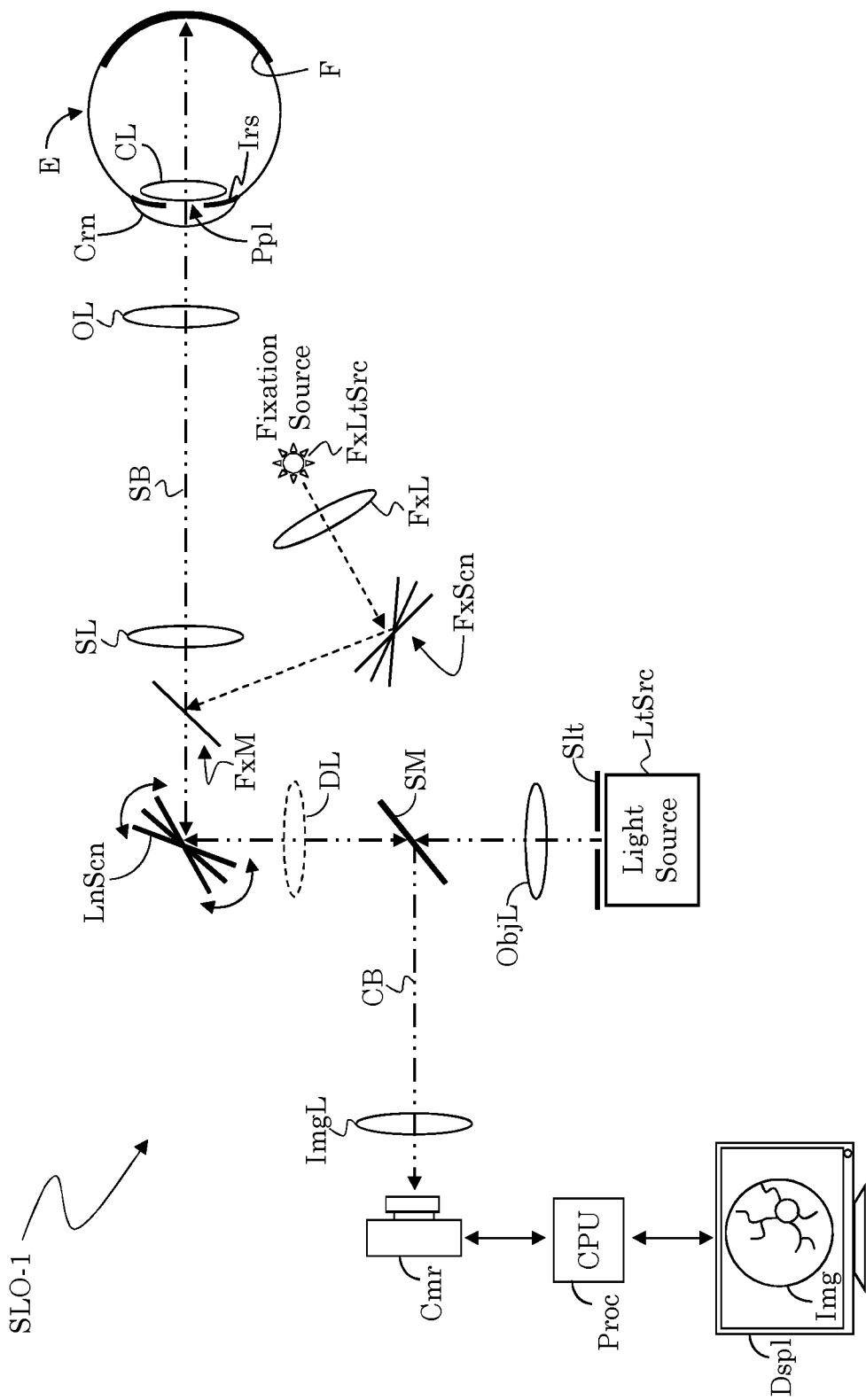
FIG. 24 illustrates an example of a slit scanning ophthalmic system for imaging a fundus.

FIG. 24 illustrates an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Crn, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state of the art lenses including but not limited to refractive, diffractive, reflective, or hybrid lenses/systems. The light from slit Slt passes through a pupil splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles), and produces scanning line beam SB with a substantially flat surface focal plane (e.g., a collimated light path). Ophthalmic lens OL may focus the scanning line beam SB onto the fundus F (or retina) of eye E and image the fundus. In this manner, scanning line beam SB creates a traversing scan line that travels across the fundus F. One possible configuration for these optics is a Kepler type telescope wherein the distance between the two lenses is selected to create an approximately telecentric intermediate fundus image (4-$f$ configuration). The ophthalmic lens OL could be a single lens, an achromatic lens, or an arrangement of different lenses. All lenses could be refractive, diffractive, reflective or hybrid as known to one skilled in the art. The focal length(s) of the ophthalmic lens OL, scan lens SL and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with another imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E are illuminated. Reflected or scattered light (or emitted light in the case of fluorescence imaging) is directed back along as similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., cancelling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgT may be positioned in the detection path to image the fundus to the camera Cmr. As is the case for objective lens ObjL, imaging lens ImgT may be any type of lens known in the art (e.g., refractive, diffractive, reflective or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system shown in FIG. 31). Thus, the collection beam (returning from all scan positions of the scanning line beam SB) is collected by the camera Cmr, and a full-frame image Img may be constructed from a composite of the individually captured collection beams, such as by montaging. However, other scanning configuration are also contemplated, including ones where the illumination beam is scanned across the eye E and the collection beam is scanned across a photo sensor array of the camera. PCT Publication WO 2012/059236 and US Patent Publication No. 2015/0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dspl, both of which can be part of the image system itself, or may be part of separate, dedicated processing and/or displaying unit(s), such as a computer system wherein data is passed from the camera Cmr to the computer system over a cable or computer network including wireless networks. The display and processor can be an all in one unit. The display can be a traditional electronic display/screen or of the touch screen type and can include a user interface for displaying information to and receiving information from an instrument operator, or user. The user can interact with the display using any type of user input device as known in the art including, but not limited to, mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 24. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is position such that it is located at the pupil plane of the system so that the light pattern on the retina/fundus can be moved depending on the desired fixation location.

Slit-scanning ophthalmoscope systems are capable of operating in different imaging modes depending on the light source and wavelength selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three color images can be combined to display the true color image, or they can be displayed individually to highlight different features of the retina. The red channel best highlights the choroid, the green channel highlights the retina, and the blue channel highlights the anterior retinal layers. Additionally, light at specific frequencies (e.g., individual colored LEDs or lasers) can be used to excite different fluorophores in the eye (e.g., autofluorescence) and the resulting fluorescence can be detected by filtering out the excitation wavelength.

The fundus imaging system can also provide an infrared (IR) reflectance image, such as by using an infrared laser (or other infrared light source). The infrared (IR) mode is advantageous in that the eye is not sensitive to the IR wavelengths. This may permit a user to continuously take images without disturbing the eye (e.g., in a preview/alignment mode) to aid the user during alignment of the instrument. Also, the IR wavelengths have increased penetration through tissue and may provide improved visualization of choroidal structures. In addition, fluorescein angiography (FA) and indocyanine green angiography (ICG) imaging can be accomplished by collecting images after a fluorescent dye has been injected into the subject's bloodstream.

Optical Coherence Tomography Imaging System

In addition to fundus photography, fundus auto-fluorescence (FAF), fluorescein angiography (FA), ophthalmic images may also be created by other imaging modalities, such as, optical coherence tomography (OCT), OCT angiography (OCTA), and/or ocular ultrasonography. The present invention, or at least portions of the present invention with minor modification(s) as it would be understood in the art, may be applied to these other ophthalmic imaging modalities. More specifically, the present invention may also be applied to ophthalmic images produces by an OCT/OCTA system producing OCT and/or OCTA images. For instance, the present invention may be applied to en face OCT/OCTA images. Examples of fundus imagers are provided in U.S. Pat. Nos. 8,967,806 and 8,998,411, examples of OCT systems are provided in U.S. Pat. Nos. 6,741,359 and 9,706,915, and examples of an OCTA imaging system may be found in U.S. Pat. Nos. 9,700,206 and 9,759,544, all of which are herein incorporated in their entirety by reference. For the sake of completeness, an exemplary OCT/OCTA system is provided herein.

Figure 25:
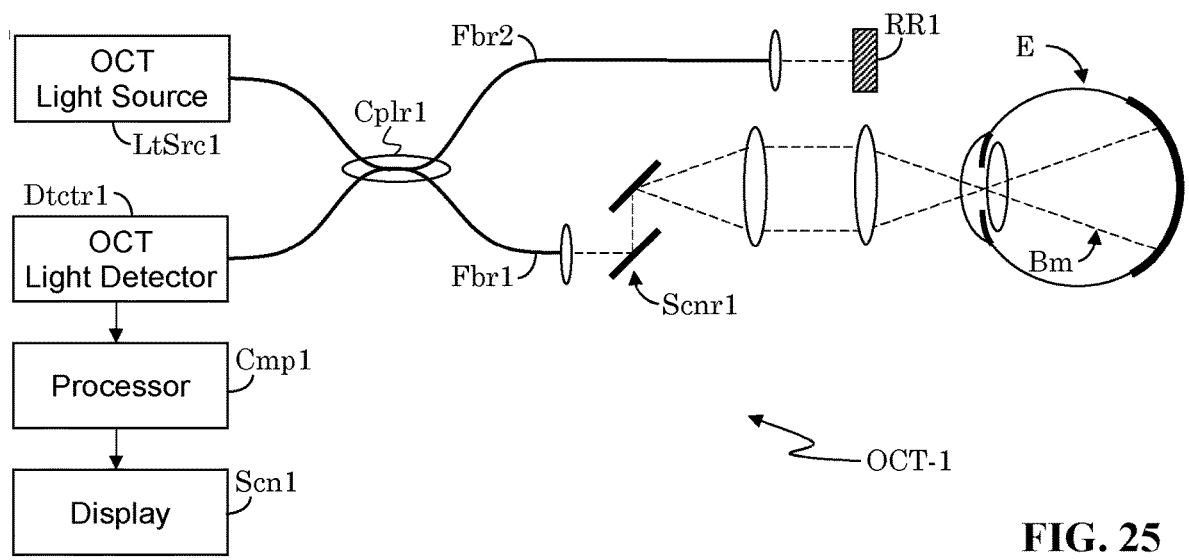
FIG. 25 illustrates a generalized frequency domain optical coherence tomography system used to collect 3-D image data of the eye suitable for use with the present invention.

FIG. 25 illustrates a generalized frequency domain optical coherence tomography (FD-OCT) system used to collect 3-D image data of the eye suitable for use with the present invention. An FD-OCT system OCT_1 includes a light source, LtSrc1. Typical light sources include, but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 can be either a broadband light source with short temporal coherence length in the case of spectral domain OCT (SD-OCT) or a wavelength tunable laser source in the case of swept source OCT (SS-OCT). The light may be scanned, typically with a scanner Scnr1 between the output of the optical fiber Fbr1 and the sample E, so that the beam of light (dashed line Bm) is scanned laterally (in x and y) over the region of the sample to be imaged. In the case of a full-field OCT, no scanner is needed and the light is applied across the entire, desired field of view (FOV) at once. Light scattered from the sample is collected, typically into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, typically in a fiber coupler Cplr1, to form light interference in an OCT light detector Dtctr1 (e.g., photodetector array, digital camera, etc.). Although a single fiber port is shown going to the detector Dtctr1, those skilled in the art will recognize that various designs of interferometers can be used for balanced or unbalanced detection of the interference signal. The output from the detector Dtctr1 is supplied to a processor Cmp1 (e.g., computing device) that converts the observed interference into depth information of the sample. The depth information may be stored in a memory associated with the processor Cmp1 and/or displayed on a display (e.g., computer/electronic display/screen) Scn1. The processing and storing functions may be localized within the OCT instrument or functions may be performed on an external processing unit (e.g., the computer system shown in FIG. 31) to which the collected data is transferred. This unit could be dedicated to data processing or perform other tasks which are quite general and not dedicated to the OCT device. The processor Cmp1 may contain, for example, a field-programmable gate array (FPGA), a digital signal processor (DSP), an application specific integrated circuit (ASIC), a graphics processing unit (GPU), a system on chip (SoC), a central processing unit (CPU), a general purpose graphics processing unit (GPGPU), or a combination thereof, that performs some, or the entire data processing steps, prior to passing on to the host processor or in a parallelized fashion.

The sample and reference arms in the interferometer could consist of bulk-optics, fiber-optics, or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography," *Optics Letters,* 36(13): 2390 2011; Y. Nakamura, et al, "High-Speed three dimensional human retinal imaging by line field spectral domain optical coherence tomography," *Optics Express,* 15(12):7103 2007; Blazkiewicz et al, "Signal-to-noise ratio study of full-field Fourier-domain optical coherence tomography," *Applied Optics,* 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to any type of OCT system or other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram, results in a complex valued OCT signal output $Aj(z)=|Aj|ei\varphi$. The absolute value of this complex OCT signal, |Aj|, reveals the profile of scattering intensities at different path lengths, and therefore scattering as a function of depth (z-direction) in the sample. Similarly, the phase, $\varphi j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. The term "cluster scan" may refer to a single unit or block of data generated by repeated acquisitions at the same (or substantially the same) location (or region) for the purposes of analyzing motion contrast, which may be used to identify blood flow. A cluster scan can consist of multiple A-scans or B-scans collected with relatively short time separations at approximately the same location(s) on the sample. Since the scans in a cluster scan are of the same region, static structures remain relatively unchanged from scan to scan within the cluster scan, whereas motion contrast between the scans that meets predefined criteria may be identified as blood flow. A variety of ways to create B-scans are known in the art including but not limited to: along the horizontal or x-direction, along the vertical or y-direction, along the diagonal of x and y, or in a circular or spiral pattern. B-scans may be in the x-z dimensions but may be any cross sectional image that includes the z-dimension.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2005/0171438, 2012/0307014, 2010/0027857, 2012/0277579 and U.S. Pat. No. 6,549,801, all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en face vasculature image is an image displaying motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

Figure 26:
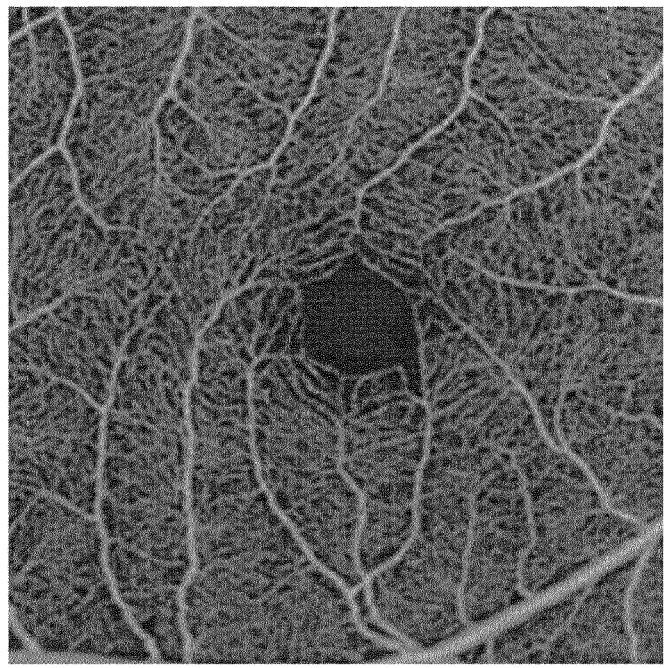
FIG. 26 shows an example of an en face vasculature image.

FIG. 26 shows an example of an en face vasculature image. After processing the data to highlight motion contrast using any of the motion contrast techniques known in the art, a range of pixels corresponding to a given tissue depth from the surface of internal limiting membrane (ILM) in retina, may be summed to generate the en face (e.g., frontal view) image of the vasculature.

Neural Networks

As discussed above, the present invention may use a neural network (NN) machine learning (ML) model. For the sake of completeness, a general discussion of neural networks is provided herein. The present invention may use any, singularly or in combination, of the below described neural network architecture(s). A neural network, or neural net, is a (nodal) network of interconnected neurons, where each neuron represents a node in the network. Groups of neurons may be arranged in layers, with the outputs of one layer feeding forward to a next layer in a multilayer perceptron (MLP) arrangement. MLP may be understood to be a feedforward neural network model that maps a set of input data onto a set of output data.

Figure 27:
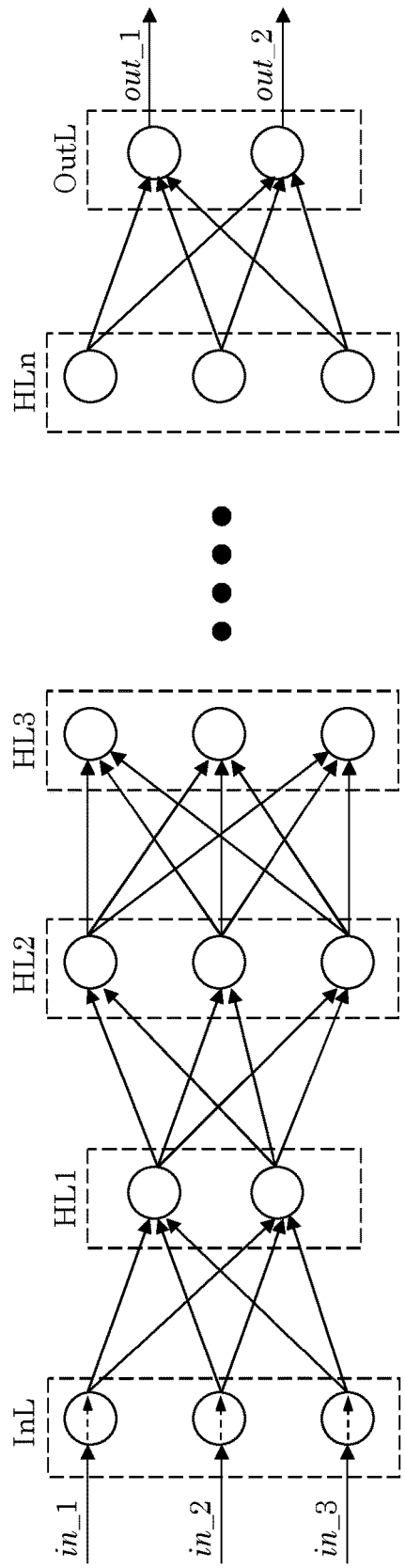
FIG. 27 illustrates an example of a multilayer perceptron (MLP) neural network.

FIG. 27 illustrates an example of a multilayer perceptron (MLP) neural network. Its structure may include multiple hidden (e.g., internal) layers HL1 to HLn that map an input layer InL (that receives a set of inputs (or vector input) in_1 to in_3) to an output layer OutL that produces a set of outputs (or vector output), e.g., out_1 and out_2. Each layer may have any given number of nodes, which are herein illustratively shown as circles within each layer. In the present example, the first hidden layer HL1 has two nodes, while hidden layers HL2, HL3, and HLn each have three nodes. Generally, the deeper the MLP (e.g., the greater the number of hidden layers in the MLP), the greater its capacity to learn. The input layer InL receives a vector input (illustratively shown as a three-dimensional vector consisting of in_1, in_2 and in_3), and may apply the received vector input to the first hidden layer HL1 in the sequence of hidden layers. An output layer OutL receives the output from the last hidden layer, e.g., HLn, in the multilayer model, processes its inputs, and produces a vector output result (illustratively shown as a two-dimensional vector consisting of out_1 and out_2).

Typically, each neuron (or node) produces a single output that is fed forward to neurons in the layer immediately following it. But each neuron in a hidden layer may receive multiple inputs, either from the input layer or from the outputs of neurons in an immediately preceding hidden layer. In general, each node may apply a function to its inputs to produce an output for that node. Nodes in hidden layers (e.g., learning layers) may apply the same function to their respective input(s) to produce their respective output(s). Some nodes, however, such as the nodes in the input layer InL receive only one input and may be passive, meaning that they simply relay the values of their single input to their output(s), e.g., they provide a copy of their input to their output(s), as illustratively shown by dotted arrows within the nodes of input layer InL.

Figure 28:
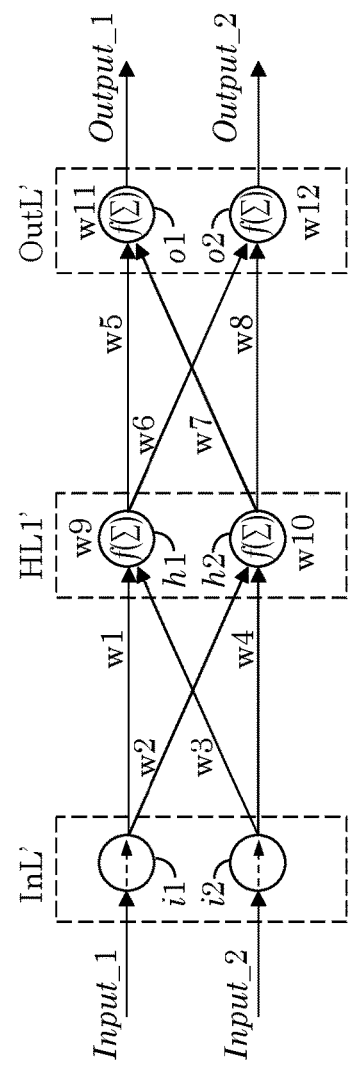
FIG. 28 shows a simplified neural network consisting of an input layer, a hidden layer, and an output layer.

For illustration purposes, FIG. 28 shows a simplified neural network consisting of an input layer InL', a hidden layer HL1', and an output layer OutL'. Input layer InL' is shown having two input nodes i1 and i2 that respectively receive inputs Input_1 and Input_2 (e.g. the input nodes of layer InL' receive an input vector of two dimensions). The input layer InL' feeds forward to one hidden layer HL1' having two nodes h1 and h2, which in turn feeds forward to an output layer OutL' of two nodes o1 and o2. Interconnections, or links, between neurons (illustrative shown as solid arrows) have weights w1 to w8. Typically, except for the input layer, a node (neuron) may receive as input the outputs of nodes in its immediately preceding layer. Each node may calculate its output by multiplying each of its inputs by each input's corresponding interconnection weight, summing the products of it inputs, adding (or multiplying by) a constant defined by another weight or bias that may be associated with that particular node (e.g., node weights w9, w10, w11, w12 respectively corresponding to nodes h1, h2, o1, and o2), and then applying a non-linear function or logarithmic function to the result. The non-linear function may be termed an activation function or transfer function. Multiple activation functions are known the art, and selection of a specific activation function is not critical to the present discussion. It is noted, however, that operation of the ML model, or behavior of the neural net, is dependent upon weight values, which may be learned so that the neural network provides a desired output for a given input.

The neural net learns (e.g., is trained to determine) appropriate weight values to achieve a desired output for a given input during a training, or learning, stage. Before the neural net is trained, each weight may be individually assigned an initial (e.g., random and optionally non-zero) value, e.g. a random-number seed. Various methods of assigning initial weights are known in the art. The weights are then trained (optimized) so that for a given training vector input, the neural network produces an output close to a desired (predetermined) training vector output. For example, the weights may be incrementally adjusted in thousands of iterative cycles by a technique termed back-propagation. In each cycle of back-propagation, a training input (e.g., vector input or training input image/sample) is fed forward through the neural network to determine its actual output (e.g., vector output). An error for each output neuron, or output node, is then calculated based on the actual neuron output and a target training output for that neuron (e.g., a training output image/sample corresponding to the present training input image/sample). One then propagates back through the neural network (in a direction from the output layer back to the input layer) updating the weights based on how much effect each weight has on the overall error so that the output of the neural network moves closer to the desired training output. This cycle is then repeated until the actual output of the neural network is within an acceptable error range of the desired training output for the given training input. As it would be understood, each training input may require many back-propagation iterations before achieving a desired error range. Typically an epoch refers to one back-propagation iteration (e.g., one forward pass and one backward pass) of all the training samples, such that training a neural network may require many epochs. Generally, the larger the training set, the better the performance of the trained ML model, so various data augmentation methods may be used to increase the size of the training set. For example, when the training set includes pairs of corresponding training input images and training output images, the training images may be divided into multiple corresponding image segments (or patches). Corresponding patches from a training input image and training output image may be paired to define multiple training patch pairs from one input/output image pair, which enlarges the training set. Training on large training sets, however, places high demands on computing resources, e.g. memory and data processing resources. Computing demands may be reduced by dividing a large training set into multiple mini-batches, where the mini-batch size defines the number of training samples in one forward/backward pass. In this case, and one epoch may include multiple mini-batches. Another issue is the possibility of a NN overfitting a training set such that its capacity to generalize from a specific input to a different input is reduced. Issues of overfitting may be mitigated by creating an ensemble of neural networks or by randomly dropping out nodes within a neural network during training, which effectively removes the dropped nodes from the neural network. Various dropout regulation methods, such as inverse dropout, are known in the art.

It is noted that the operation of a trained NN machine model is not a straight-forward algorithm of operational/analyzing steps. Indeed, when a trained NN machine model receives an input, the input is not analyzed in the traditional sense. Rather, irrespective of the subject or nature of the input (e.g., a vector defining a live image/scan or a vector defining some other entity, such as a demographic description or a record of activity) the input will be subjected to the same predefined architectural construct of the trained neural network (e.g., the same nodal/layer arrangement, trained weight and bias values, predefined convolution/deconvolution operations, activation functions, pooling operations, etc.), and it may not be clear how the trained network's architectural construct produces its output. Furthermore, the values of the trained weights and biases are not deterministic and depend upon many factors, such as the amount of time the neural network is given for training (e.g., the number of epochs in training), the random starting values of the weights before training starts, the computer architecture of the machine on which the NN is trained, selection of training samples, distribution of the training samples among multiple mini-batches, choice of activation function(s), choice of error function(s) that modify the weights, and even if training is interrupted on one machine (e.g., having a first computer architecture) and completed on another machine (e.g., having a different computer architecture). The point is that the reasons why a trained ML model reaches certain outputs is not clear, and much research is currently ongoing to attempt to determine the factors on which a ML model bases its outputs. Therefore, the processing of a neural network on live data cannot be reduced to a simple algorithm of steps. Rather, its operation is dependent upon its training architecture, training sample sets, training sequence, and various circumstances in the training of the ML model.

In summary, construction of a NN machine learning model may include a learning (or training) stage and a classification (or operational) stage. In the learning stage, the neural network may be trained for a specific purpose and may be provided with a set of training examples, including training (sample) inputs and training (sample) outputs, and optionally including a set of validation examples to test the progress of the training. During this learning process, various weights associated with nodes and node-interconnections in the neural network are incrementally adjusted in order to reduce an error between an actual output of the neural network and the desired training output. In this manner, a multi-layer feed-forward neural network (such as discussed above) may be made capable of approximating any measurable function to any desired degree of accuracy. The result of the learning stage is a (neural network) machine learning (ML) model that has been learned (e.g., trained). In the operational stage, a set of test inputs (or live inputs) may be submitted to the learned (trained) ML model, which may apply what it has learned to produce an output prediction based on the test inputs.

Like the regular neural networks of FIGS. 26 and 27, convolutional neural networks (CNN) are also made up of neurons that have learnable weights and biases. Each neuron receives inputs, performs an operation (e.g., dot product), and is optionally followed by a non-linearity. The CNN, however, may receive raw image pixels at one end (e.g., the input end) and provide classification (or class) scores at the other end (e.g., the output end). Because CNNs expect an image as input, they are optimized for working with volumes (e.g., pixel height and width of an image, plus the depth of the image, e.g., color depth such as an RGB depth defined of three colors: red, green, and blue). For example, the layers of a CNN may be optimized for neurons arranged in 3 dimensions. The neurons in a CNN layer may also be connected to a small region of the layer before it, instead of all of the neurons in a fully-connected NN. The final output layer of a CNN may reduce a full image into a single vector (classification) arranged along the depth dimension.

Figure 29:
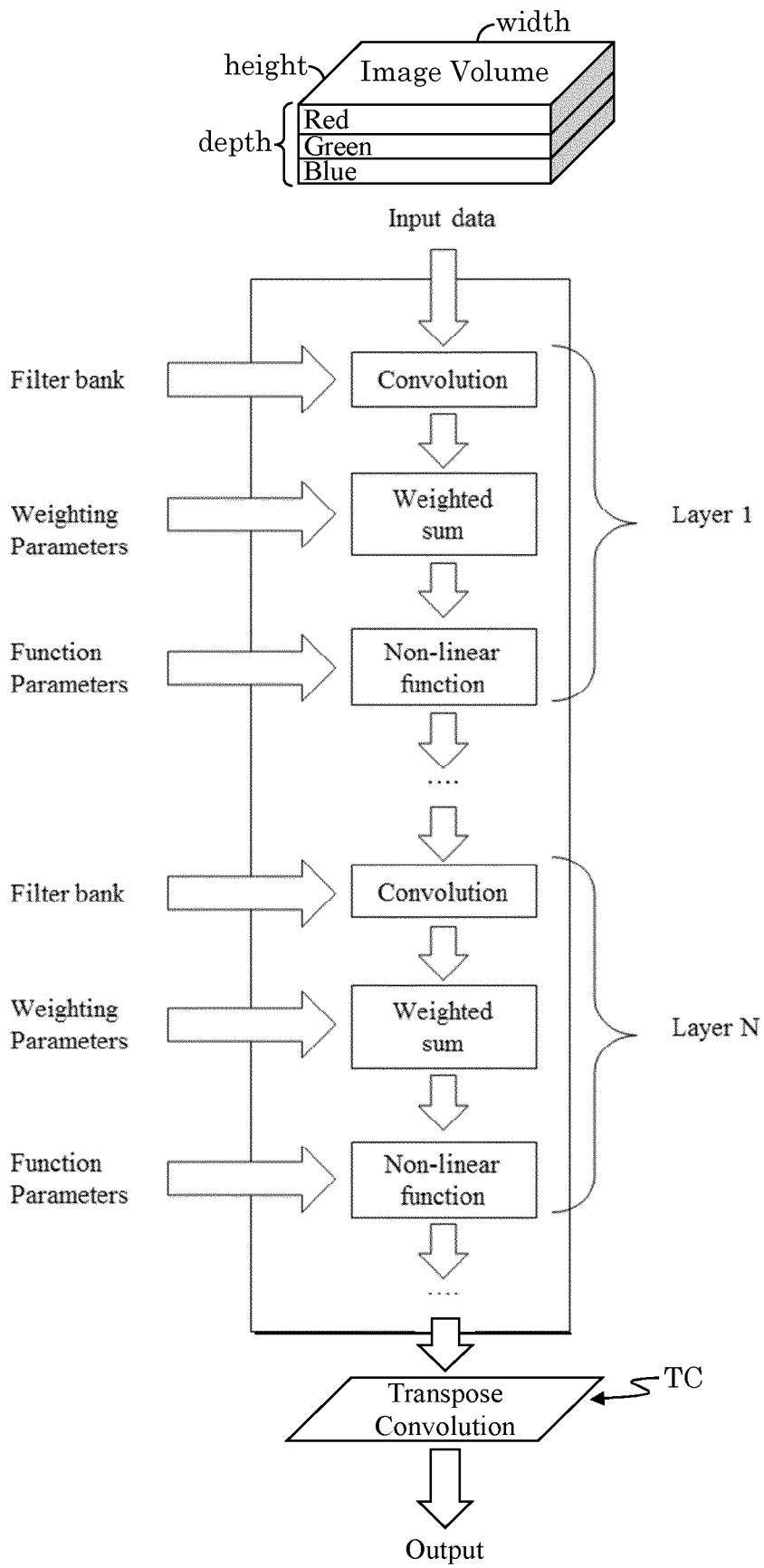
FIG. 29 illustrates an example convolutional neural network architecture.

FIG. 29 provides an example convolutional neural network architecture. A convolutional neural network may be defined as a sequence of two or more layers (e.g., Layer 1 to Layer N), where a layer may include a (image) convolution step, a weighted sum (of results) step, and a non-linear function step. The convolution may be performed on its input data by applying a filter (or kernel), e.g. on a moving window across the input data, to produce a feature map. Each layer and component of a layer may have different predetermined filters (from a filter bank), weights (or weighting parameters), and/or function parameters. In the present example, the input data is an image, which may be raw pixel values of the image, of a given pixel height and width. In the present example, the input image is illustrated as having a depth of three color channels RGB (Red, Green, and Blue). Optionally, the input image may undergo various preprocessing, and the preprocessing results may be input in place of, or in addition to, the raw input image. Some examples of image preprocessing may include: retina blood vessel map segmentation, color space conversion, adaptive histogram equalization, connected components generation, etc. Within a layer, a dot product may be computed between the given weights and a small region they are connected to in the input volume. Many ways of configuring a CNN are known in the art, but as an example, a layer may be configured to apply an elementwise activation function, such as max (0, x) thresholding at zero. A pooling function may be performed (e.g., along the x-y directions) to down-sample a volume. A fully-connected layer may be used to determine the classification output and produce a one-dimensional output vector, which has been found useful for image recognition and classification. However, for image segmentation, the CNN would need to classify each pixel. Since each CNN layers tends to reduce the resolution of the input image, another stage is needed to up-sample the image back to its original resolution. This may be achieved by application of a transpose convolution (or deconvolution) stage TC, which typically does not use any predefine interpolation method, and instead has learnable parameters.

Convolutional Neural Networks have been successfully applied to many computer vision problems. As explained above, training a CNN generally requires a large training dataset. The U-Net architecture is based on CNNs and can generally be trained on a smaller training dataset than conventional CNNs.

Figure 30:
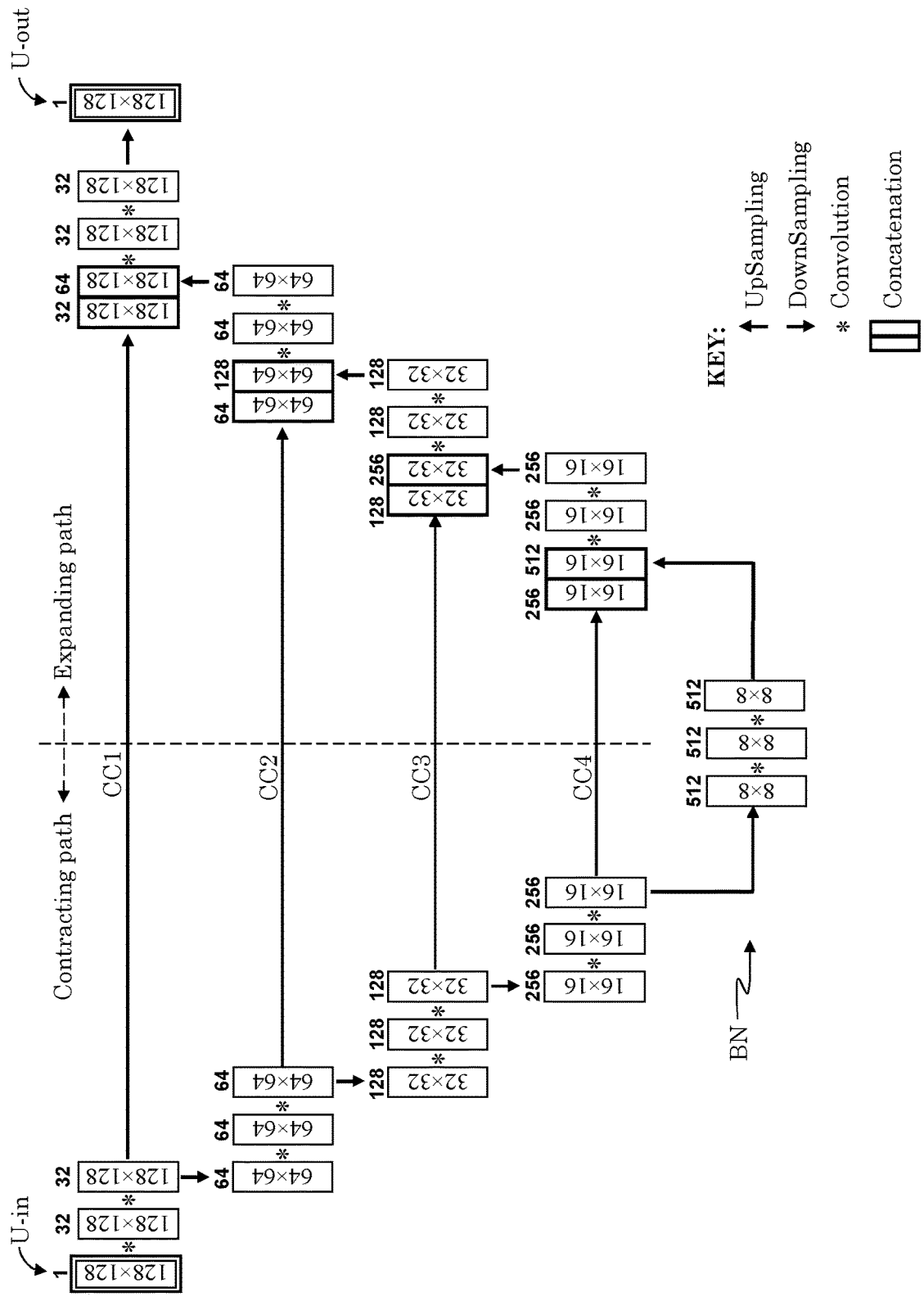
FIG. 30 illustrates an example U-Net architecture.

FIG. 30 illustrates an example U-Net architecture. The present exemplary U-Net includes an input module (or input layer or stage) that receives an input U-in (e.g., input image or image patch) of any given size (e.g., 128 by 128 pixels in size). The input image may be a fundus image, an OCT/OCTA en face, B-scan image, etc. It is to be understood, however, that the input may be of any size and dimension. For example, the input image may be an RGB color image, monochrome image, volume image, etc. The input image undergoes a series of processing layers, each of which is illustrated with exemplary sizes, but these sizes are illustration purposes only and would depend, for example, upon the size of the image, convolution filter, and/or pooling stages. The present architecture consists of a contracting path (comprised of four encoding modules) followed by an expanding path (comprised of four decoding modules), and four copy-and-crop links (e.g., CC1 to CC4) between corresponding modules/stages that copy the output of one encoding modules in the contracting path and concatenates it to the input of a correspond decoding module in the expanding path. This results in a characteristic U-shape, from which the architecture draws its name. The contracting path is similar to an encoder, and its basic function is to capture context via compact feature maps. In the present example, each encoding modules in the contracting path includes two convolutional neural network layers, which may be followed by one max pooling layer (e.g., Down-Sampling layer). For example, input image U_in undergoes two convolution layers, each with 32 feature maps. The number of feature maps may double at each pooling, starting with 32 feature maps in the first block, 64 in the second, and so on. The contracting path thus forms a convolutional network consisting of a plurality of encoding modules (or stages), each providing a convolution stage, followed by an activation function (e.g., a rectified linear unit, ReLU or sigmoid layer) and a max pooling operation. The expanding path is similar to a decoder, and its function is to provide localization and to retain spatial information despite the down sampling and any max-pooling performed in the contracting stage. In the contracting path, spatial information is reduced while feature information is increased. The expanding path includes a plurality of decoding modules, where each decoding module concatenates its current value with the output of a corresponding encoding module. That is, the feature and spatial information are combined in the expanding path through a sequence of up-convolutions (e.g., UpSampling or transpose convolutions or deconvolutions) and concatenations with high-resolution features from the contracting path (e.g., via CC1 to CC4). Thus, the output of a deconvolution layer is concatenated with the corresponding (optionally cropped) feature map from the contracting path, followed by two convolutional layers and activation function (with optional batch normalization). The output from the last module in the expanding path may be fed to another processing/training block or layer, such as a classifier block, that may be trained along with the U-Net architecture.

The module/stage (BN) between the contracting path and the expanding path may be termed the "bottleneck." The bottleneck BN may consist of two convolutional layers (with batch normalization and optional dropout).

Computing Device/System

Figure 31:
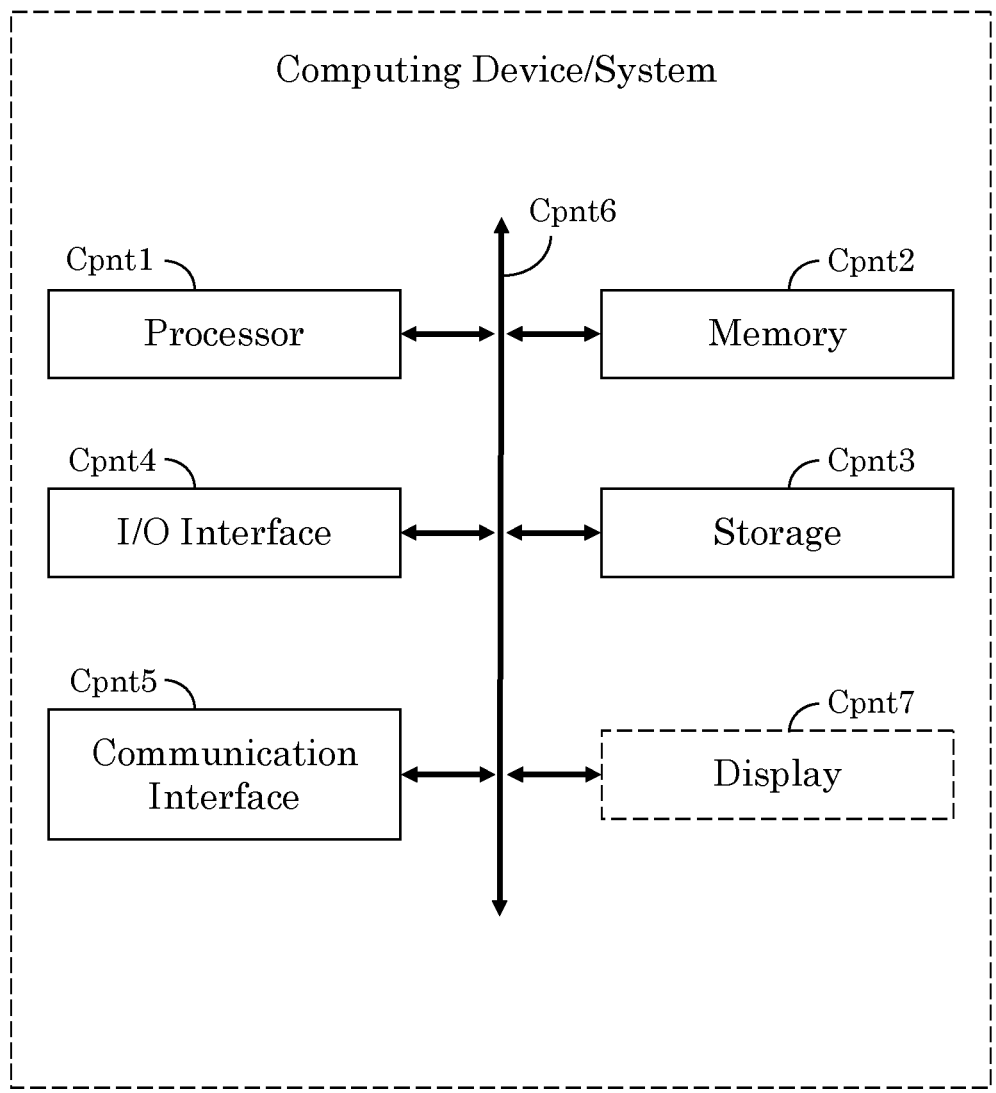
FIG. 31 illustrates an example computer system (or computing device or computer device).

FIG. 31 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number internal registers, and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to computer system, and include one or more of a disk drive (e.g., hard disk drive, HDD, or solid state drive, SSD), flash memory, ROM, EPROM, optical disc, a magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. A method for determining a defocus measure of an ophthalmic imaging system, the method comprising:
    illuminating a first region of a retina of an eye;
    collecting a first image of light returning from the first region on a detector;
    illuminating a second region of the retina of the eye, the second region partially overlapping the first region;
    collecting a second image of light returning from the second region on the detector;
    defining a third image by taking an intensity difference of the first image and the second image,
    wherein the third image includes a linear region;
    determining a width measure of the linear region;
    determining the defocus measure based on the width measure;
    fitting a Gaussian shape to the linear region of the third image; and
    determining the width measure at least in part based on the fitted Gaussian shape.

2. The method of claim 1, wherein the width measure is based on a second order moment of an intensity distribution of the third image.

3. The method of claim 1, further comprising segmenting the third image into a foreground segment and a background segment, wherein the width measure is determined from the foreground segment.

4. The method of claim 1, wherein:
    the first region is illuminated with a first line of illumination having a first width along a width dimension;
    the second region is illuminated with a second line of illumination having the first width along the width dimension;
    the second region is offset from the first region along the width dimension; and
    the width of the linear region of the third image is defined by the offset of the second region from the first region along the width dimension.

5. The method of claim 1, wherein:
    taking the intensity difference of the first image and second image produces a positive linear image and a negative linear image; and
    one of the positive linear image and negative linear image is selected as the linear region of the third image.

6. The method of claim 1, wherein the ophthalmic imaging system is a fundus camera.

7. A method for determining a defocus measure of an ophthalmic imaging system, the method comprising:
    illuminating a first region of a retina of an eye;
    collecting a first image of light returning from the first region on a detector;
    illuminating a second region of the retina of the eye, the second region partially overlapping the first region;
    collecting a second image of light returning from the second region on the detector;
    defining a third image by taking an intensity difference of the first image and the second image,
    wherein the third image includes a linear region;
    determining a width measure of the linear region;
    determining the defocus measure based on the width measure; and
    improving the resolution of the third image by applying the following process:

$$\Sigma w_i \text{Image} = (((\Sigma w_i \, \Pi_i) \cdot O) * p_{detect}$$

wherein Image is the observed intensities, $p_{illum}$ is the point spread function of the illumination, $p_{detect}$ is the point spread function of the detection, $\Pi$ is the rectangular stripe of the illumination, asterisk "*" denotes convolution, and dot "·" denotes multiplication.

8. A method for determining a defocus measure of an ophthalmic imaging system, the method comprising:
    illuminating a first region of a retina of an eye;

collecting a first image of light returning from the first region on a detector;
illuminating a second region of the retina of the eye, the second region partially overlapping the first region;
collecting a second image of light returning from the second region on the detector;
defining a third image by taking an intensity difference of the first image and the second image,
wherein the third image includes a linear region;
determining a width measure of the linear region;
determining the defocus measure based on the width measure;
improving the resolution of the third image by first approximating a sine illumination using weight as follows:

$$\Sigma w_i \sqcap_i \approx \sin_i$$

wherein $w_i$ are weights and $\sqcap$ is the rectangular shape stripe of the illumination;
then defining $$\Sigma w_i \text{Image} = \alpha_i(((\sin_i)) \cdot O) * p_{detect}$$

wherein Image is the observed intensities, alpha $\alpha_i$ are scaling factors, $p_{detect}$ is the point spread function of the detection, asterisk "*" denotes convolution, and dot "." denotes multiplication;
removing the alpha $\alpha_i$ scaling factors by intensity normalization; and
recombining the sinusoids.

9. A method for determining a defocus measure of an ophthalmic imaging system, the method comprising:
illuminating a first region of a retina of an eye;
collecting a first image of light returning from the first region on a detector;
illuminating a second region of the retina of the eye, the second region partially overlapping the first region;
collecting a second image of light returning from the second region on the detector;
defining a third image by taking an intensity difference of the first image and the second image,
wherein the third image includes a linear region;
determining a width measure of the linear region;
determining the defocus measure based on the width measure; and
determining topography information of the retina based on the light intensity center of mass of the linear region of the third image.

10. The method of claim 9, wherein the topography information is determined for a retinal region defined by the length of the rectangular shape part of the third image by following a change in position of the light intensity center of mass along the length of the rectangular shape part.

11. The method of claim 9, further including segmenting vessels, segmenting the optical disk, or determining a tumor volume based on the topography information.

* * * * *